(12) United States Patent
Forster et al.

(10) Patent No.: US 7,872,129 B2
(45) Date of Patent: *Jan. 18, 2011

(54) COMPOSITIONS USEFUL AS INHIBITORS OF GSK-3

(75) Inventors: Cornelia J. Forster, Pelham, NH (US); Larry C. Park, Waltham, MA (US); Marion W. Wannamaker, Bolton, MA (US); Yung-Mae M. Yao, Newton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/338,129

(22) Filed: Dec. 18, 2008

(65) Prior Publication Data

US 2009/0118278 A1 May 7, 2009

Related U.S. Application Data

(62) Division of application No. 10/632,340, filed on Aug. 1, 2003, now Pat. No. 7,491,730.

(60) Provisional application No. 60/400,967, filed on Aug. 2, 2002.

(51) Int. Cl.
C07D 403/12 (2006.01)
C07D 403/14 (2006.01)
C07D 417/14 (2006.01)
A61K 31/4162 (2006.01)
A61K 31/506 (2006.01)
A61K 31/5377 (2006.01)
A61P 3/10 (2006.01)
A61P 9/10 (2006.01)
A61P 25/18 (2006.01)

(52) U.S. Cl. ............... 544/328; 544/122; 514/256; 514/275; 514/234.5; 514/252.18

(58) Field of Classification Search ............... 544/328, 544/122; 514/256, 275, 234.5, 252.18
See application file for complete search history.

(56) References Cited

U.S. PATENT DOCUMENTS

| | | | |
|---|---|---|---|
| 3,755,322 A | 8/1973 | Winter et al. | |
| 4,540,698 A | 9/1985 | Ishikawa et al. | |
| 4,711,951 A | 12/1987 | Axen et al. | |
| 5,124,441 A | 6/1992 | Carlsson et al. | |
| 6,093,716 A | 7/2000 | Davis et al. | |
| 6,184,226 B1 | 2/2001 | Chakravarty et al. | |
| 6,277,989 B1 | 8/2001 | Chakravarty et al. | |
| 6,495,582 B1 | 12/2002 | Hale et al. | |
| 6,528,509 B1 | 3/2003 | Hale et al. | |
| 6,558,657 B1 | 5/2003 | Mandeville, III et al. | |
| 6,562,971 B2 | 5/2003 | Frauenkron et al. | |
| 6,579,983 B1 | 6/2003 | Batchelor et al. | |
| 6,589,958 B1 | 7/2003 | Frietze | |
| 6,610,677 B2 | 8/2003 | Davies et al. | |
| 6,613,776 B2 | 9/2003 | Knegtel et al. | |
| 6,638,926 B2 | 10/2003 | Davies et al. | |
| 6,653,300 B2 | 11/2003 | Bebbington et al. | |
| 6,653,301 B2 | 11/2003 | Bebbington et al. | |
| 6,656,939 B2 | 12/2003 | Bebbington et al. | |
| 6,660,731 B2 | 12/2003 | Bebbington et al. | |
| 6,664,247 B2 | 12/2003 | Bebbington et al. | |
| 6,696,452 B2 * | 2/2004 | Davies et al. | 514/256 |
| 6,727,251 B2 | 4/2004 | Bebbington et al. | |
| 6,841,579 B1 | 1/2005 | Plowman et al. | |
| 6,846,928 B2 | 1/2005 | Bebbington et al. | |
| 6,989,385 B2 | 1/2006 | Bebbington et al. | |
| 7,008,948 B2 | 3/2006 | Bebbington et al. | |
| 7,087,603 B2 | 8/2006 | Bebbington et al. | |
| 7,091,343 B2 | 8/2006 | Bebbington et al. | |
| 7,098,330 B2 | 8/2006 | Bebbington et al. | |
| 7,115,739 B2 | 10/2006 | Bebbington et al. | |
| 7,179,826 B2 | 2/2007 | Bebbington et al. | |
| 7,491,730 B2 * | 2/2009 | Forster et al. | 514/275 |

(Continued)

FOREIGN PATENT DOCUMENTS

EP 0019811 12/1980

(Continued)

OTHER PUBLICATIONS

Doble et al., Journal of Cell Science, 116, 1175-1186, 2003.*

(Continued)

*Primary Examiner*—Venkataraman Balasubramanian
(74) *Attorney, Agent, or Firm*—Jennifer G. Che

(57) ABSTRACT

The present invention provides a compound of formula I:

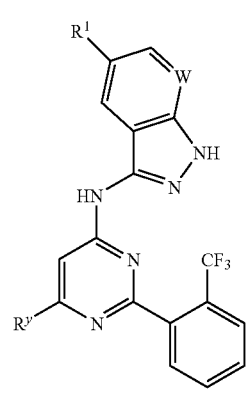

or a pharmaceutically acceptable derivative thereof. These compounds are inhibitors of protein kinases, particularly inhibitors of GSK3 mammalian protein kinase. The invention also provides pharmaceutically acceptable compositions comprising the compounds of the invention and methods of utilizing those compounds and compositions in the treatment of various protein kinase mediated disorders.

14 Claims, 2 Drawing Sheets

U.S. PATENT DOCUMENTS

| | | |
|---|---|---|
| 2001/0018436 A1 | 8/2001 | Cushing et al. |
| 2002/0052386 A1 | 5/2002 | Armistead et al. |
| 2002/0065270 A1 | 5/2002 | Moriarty et al. |
| 2003/0004161 A1 | 1/2003 | Bebbington et al. |
| 2003/0064981 A1 | 4/2003 | Knegtel et al. |
| 2003/0069239 A1 | 4/2003 | Cai et al. |
| 2003/0069248 A1 | 4/2003 | Chakravarty et al. |
| 2003/0078166 A1 | 4/2003 | Davies et al. |
| 2003/0087922 A1 | 5/2003 | Bethiel et al. |
| 2003/0092714 A1 | 5/2003 | Cao et al. |
| 2003/0096813 A1 | 5/2003 | Cao et al. |
| 2003/0096816 A1 | 5/2003 | Cao et al. |
| 2003/0144309 A1 | 7/2003 | Choon-Moon |
| 2003/0171389 A1 | 9/2003 | Bemis et al. |
| 2003/0187002 A1 | 10/2003 | Mortlock et al. |
| 2003/0199526 A1 | 10/2003 | Choquette et al. |
| 2003/0207873 A1 | 11/2003 | Harrington |
| 2004/0002496 A1 | 1/2004 | Bebbington et al. |
| 2004/0009996 A1 | 1/2004 | Moon et al. |
| 2004/0023963 A1 | 2/2004 | Cao et al. |
| 2004/0029857 A1 | 2/2004 | Hale et al. |
| 2004/0097531 A1 | 5/2004 | Ledeboer et al. |
| 2004/0157893 A1 | 8/2004 | Bebbington et al. |
| 2004/0229875 A1 | 11/2004 | Cao et al. |
| 2005/0038023 A1 | 2/2005 | Bebbington et al. |
| 2005/0234059 A1 | 10/2005 | Hale et al. |
| 2006/0270660 A1 | 11/2006 | Charrier et al. |

FOREIGN PATENT DOCUMENTS

| | | |
|---|---|---|
| EP | 136976 | 4/1985 |
| EP | 0302312 | 2/1989 |
| GB | 2052487 | 1/1981 |
| JP | 10-130150 | 5/1998 |
| JP | 06-65237 | 10/2007 |
| WO | 9208715 | 5/1992 |
| WO | 9509851 | 4/1995 |
| WO | 9515758 | 6/1995 |
| WO | 9709325 | 3/1997 |
| WO | 9719065 | 5/1997 |
| WO | 9802434 | 1/1998 |
| WO | 9811095 | 3/1998 |
| WO | 9816502 | 4/1998 |
| WO | 9918781 | 4/1999 |
| WO | 9941253 | 8/1999 |
| WO | 9947154 | 9/1999 |
| WO | 9965897 | 12/1999 |
| WO | 0012497 | 3/2000 |
| WO | 0038675 | 7/2000 |
| WO | 0059509 | 10/2000 |
| WO | 0078757 | 12/2000 |
| WO | 0112621 | 2/2001 |
| WO | 0125220 | 4/2001 |
| WO | 0139777 | 6/2001 |
| WO | 0140215 | 6/2001 |
| WO | 0144242 | 6/2001 |
| WO | 0147879 | 7/2001 |
| WO | 0164655 | 9/2001 |
| WO | 0250066 | 6/2002 |
| WO | 02079197 | 10/2002 |
| WO | 0224667 | 3/2003 |
| WO | 0247690 | 6/2003 |
| WO | 2004000833 | 12/2003 |
| WO | 2004013140 | 2/2004 |
| WO | 9614843 | 7/2008 |

OTHER PUBLICATIONS

Charpiot, B. et al., "Quinazolines: Combined type 3 and 4 phosphodiesterase inhibitors", Bioorg. Med. Chem. Lett, 8 (20), 2891-2896 (1998).

Shikhaliev, K.S. et al., "Heterocyclization of quinazol-2-ylguanidines. 1. Reaction with amino acids", Chem. Heterocycl. Compd., 35 (7), 818-820 (1999).

Singh, S.P. et al., "Synthesis & Mass Spectra of Some Substituted 2-(2'-Benzazolylamino)pyrimidines", Indian J. Chem. Sect. B, 22(1); 37-42 (1983).

Ti, J. et al., "Anticandidal activity of pyrimidine-peptide conjugates", J. Med. Chem., 23(8), 913-918 (1980).

Kretzschmar, E. et al., "Synthese von 2,6-disubstituierten 4-Hydroxy-5,6,7,8-tetrahydropyrido[4,3-d]pyrimidinen", Pharmazie, 43(7), 475-476 (1988).

Norman, M.H. et al., "Structure-Activity Relationships of a Series of Pyrrolo[3,2-d]pyrimidine Derivatives and Related Compounds as Neuropeptide Y5 Receptor Antagonists", J. Med. Chem., 43(22), 4288-4312 (2000).

Nugent, R.A. et al., "Pyrimidine Thioethers: A Novel Class of HIV-1 Reverse Transcriptase Inhibitors with Activity Against BHAP-Resistant HIV", J. Med. Chem., 41, 3793-3803 (1998).

Myers, M.R. et al., "The synthesis and SAR of new 4-(N-alkyl-N-phenyl)amino-6,7-dimethoxyquinazolines and 4-(N-alkyl-N-phenyl)aminopyrazolo[3,4-d]pyrimidines, inhibitors of CSF-1R tyrosine kinase activity", Bioorg. Med. Chem. Lett., 7, 4, 421-424 (1997).

Agarwal, N. et al., "Suitably functionalised pyrimidines as potential antimycotic agents", Bioorg. Med. Chem. Lett., 10, 8, 703-706 (2000).

Crespo, M.I. et al., "Design, Synthesis, and Biological Activities of New Thieno[3,2-d]pyrimidines as Selective Type 4 Phosphodiesterase Inhibitors", J. Med. Chem., 41 (21), 4021-4035 (1998).

Noell, C.W. et al., "Potential Purine Antagonists. XX. The Preparation and Reactions of Some Methylthiopurines", J. Am. Chem. Soc., 81(22), 5997-6007 (1959).

Lubbers, T. et al., "Design, synthesis, and structure—activity relationship studies of ATP analogues as DNA gyrase inhibitors", Bioorg. Med. Chem. Lett., 10,8, 821-826 (2000).

D'Atri, G. et al., "Novel pyrimidine and 1,3,5-triazine hypolipemic agents", J. Med. Chem. 27(12), 1621-1629 (1984).

Venugopalan, B. et al., "Synthesis and antimalarial activity of pyrido[3,2-f]quinozalines and their oxides", Indian J. Chem. Sect. B, 34, 9, 778-790 (1995).

Curd, F.H.S. et al, "Synthetic antimalarials. Part XVII. Some aminoalkylaminoquinoline derivatives", J. Chem. Soc., 899-909 (1947).

Haworth, R.D. et al., "Synthetic antimalarials. Part XXVII. Some derivatives of phthalazine, quinoxaline, and isoquinoline", J. Chem. Soc., 777-782 (1948).

Nair, M.D., et al., "3-Chloroisocarbostyril & Its Chlorination Products", Indian J. Chem., 467-470 (1967).

Jeffery, J.E. et al., "Synthesis of sibutramine, a novel cyclobutylalkylamine useful in the treatment of obesity, and its major human metabolites", J. Chem. Soc., Perkin Trans. 1, 21, 2583-2589 (1996).

Gnecco, D. et al., "An Improved Preparation of 1-Methyl-4-Cyano-4-phenylpiperidine", Org. Prep. Proced. Int., 18 (4), 478-480 (1996).

Fedorynski, M. et al., "Synthesis of 1-Arycyclopropanecarbonitriles under Phase-transfer Catalytic Conditions", Org. Prep. Proced. Int., 27(3), 355-359 (1995).

Suzuki, S. et al., "Application of electrogenerated triphenylmethyl anion as a base for alkylation of arylacetic esters and arylacetonitriles and isomerization of allylbenzenes", Can. J. Chem., 72(2): 357-361 (1994).

Prasad, G. et al., "18-Crown-6 as a catalyst in the dialkylation of o-nitrophenacyl derivatives", J. Org. Chem., 25, 7188-7190 (1991).

Moss, R.A. et al., "Conversion of 'Obstinate' Nitriles to Amidines by Garigipati's Reaction", Tetrahedron Lett., 36(48), 8761-8764 (1995).

Garigipati, R.S., "An efficient conversion of nitriles to amidines", Tetrahedron Lett., 31(14), 1969-1972 (1990).

Warner, S.L. et al, "Targeting Aurora-2 Kinase in Cancer," Mol. Cancer Thera., 2, 589-585, 2003.

Wagman, A.S. et all, "Discovery and Development of GSK3 Inhibitors for the Treatment of Type 2 Diabetes," Current Pharmaceutical Design, 10, 1105-1137 (2004).

Nezu, Y. et al., "Dimethoxypyrimidines as Novel Herbicides. Part 2. Synthesis and Herbicidal Activity of Dimethoxyphenoxyphenoxypyrimidines and Analogues," Pestic. Sci., 47: 115-124 (1996).

Tanaka, T.U. et al., "Evidence that the Ipl1-Sli15 (Aurora Kinase-INCENP) Complex Promotes Chromosome Bi-orientation by Altering Kinetochore-Spindle Pole Connections," Cell, 108, 317-329 (2002).

Soriano, P. et al., "Targeted Disruption of the C-SIC Pmto-Oncogene Leads to Osteopetrosis in Mice," Cell, 64: 693-702, (1991).

Campbell, S.F. et al., "2,4-Diamino-6,7-dimethoxyquinazolines. 3.2-(4-Heterocyclylpiperazin-l-yl) Derivatives as α1-Adrenoceptor Antagonists and Antihypertensive Agents," J. Med. Chem., 30, 1794-1798 (1987).

Casanova, B. et al., "Revision critica de la patogenia actual de la esclerosis múltiple y futuras direcciones posibles," Rev. Neurol., 28 (9): 909-915 (1999).

Simone, J.V., "Oncology: Introduction" in Cecil Textbook in Medicine, 20th ed., vol. 1, 1004-1010 (1996).

Coleman, R.A., "The Biological Evaluation of New Compounds" in Medicinal Chemistry: Principles and Practice, King, Frank D. ed, Royal Society of Chemistry, 53-66 (1994).

The Condensed Chemical Dictionary, Sixth Edition by Arthur and Elizabeth Rose, 38 (1961).

Damasio, A.R., "Alzheimer's Disease and Related Dementia," in Cecil Textbook of Medicine, 20th ed., 2: 1992-1996 (1996).

Rogers, E. et al., "The aurora kinase AIR-2 functions in the release of chromosome cohesion in Caenorhabditis elegans meiosis," J. Cell Biol., 157(2): 219-229 (2002).

Fisher A., "Therapeutic Strategies in Alzheimer's Disease: M1 Muscarinic Agonists," Jpn. J. Pharmacol., 84(2):101-12 (2000).

Frame, M.C., "Src in cancer: deregulation and consequences for cell behaviour," Biochimica et Biophysica Acta., 1602, 114-130 (2002).

Frampton, J.E. et al., "Pentoxifylline (Oxpentifylline)—A Review of its Therapeutic Efficacy in the Management of Peripheral Vascular and Cerebrovascular Disorder," Drugs & Aging, 7(6): 480-503 (1995).

Ganellin, C.R., "Past Approaches to Discovering New Drugs as Medicines" in Medicinal Chemistry, Principles and Practices. King, Frank D. ed, Royal Society of Chemistry, 189-205 (1994).

Hamdane, M. et al., "A Therapeutic Target in Alzheimer Neurodegeneration," J. Mol. Neurosci., 19(3): 275-87 (2002).

Hardt, S.E. et al., "Glycogen Synthase Kinase-3β—A Novel Regulator of Cardiac Hypertrophy and Development," Circulation Research, 90: 1055-1063 (2002).

Heaney, F. et al., "Pyrimidine annelated heterocycles—synthesis and cycloaddition of the first pyrimido[1,4]diazepine N-oxides," J. Chem. Soc., Perkin Trans 1,622-632 (2001).

Hendriksen, E.J. et al., "Modulation of muscle insulin resistance by selective inhibition of GSK-3 in Zucker diabetic fatty rats," Am. J. Physiol. Endocrinol. Metab., 284: E892-E900 (2003).

Okafor, C.O., "Studies in the Heterocyclic Series. X. 1,3,9-Triazaphenothiazine Ring System, a New Phenothiazine Ring," J. Org. Chem., 40(19): 2753-2755 (1975).

Jambhekar, S.S., "Biopharmaceutical Properties of Drug Substances" in Principles of Medicinal Chemistry, 4th ed., 12-24, (1995).

Layzer, R.B., "Section Five—Degenerative Diseases of the Nervous System" in Cecil Textbook of Medicine, 20th ed., 2: 2050-2057 (1996).

Lee, S.J. et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities," J. Med . Chem., 38 (18): 3547-3557 (1995).

Nezu, Y. et al., "Dimethoxypyrimidines as Novel Herbicides. Part 1. Synthesis and Herbicidal Activity of Dimethoxyphenoxyphenoxypyrimidines and Analogues," Pestic. Sci., 47: 103-113 (1996).

Cohen, P., "Dissection of the Protein Phosphorylation Cascades Involved in Insulin and Growth Factor Action", Biochem. Soc. Trans., 21, 555-567 (1993).

Alonso, M. et al., "GSK-3 Inhibitors: Discoveries and Developments", Current Medicinal Chemistry, 11, 755-763 (2004).

Anonymous, "Vertex Inhbitors of Aurora-2, glycogen synthase kinase-3 and Src Kinase", Expert Opin. Ther. Patents, 14(3): 439-443 (2004).

Baig, G.U. et al., "Triazines and Related Products. Part 28' Conversion of 3-Aryl-l-(2-cyanopheny1) triazenes into 3-Arylqu i nazol i n-4(3H)—ones with Formamide" J. Chem. Soc. Perkin Trans. I, 3765-2766 (1984).

Bischoff, J.R., et al., "A homologue of Drosophila aurora kinase is oncogenic and amplified in human colorectal cancers", The EMBO Journal, 17(11): 3052-3065 (1998).

Bischoff, J.R., et al., "The Aurora/lpl1p kinase family: regulators of chromosome segregation and cytokinesis", Cell Biology, 9, 454-459 (1999).

Brunswick, D.J. et al., "Cyclic Amidines. Part XXII. Novel Isomerism of Disubstituted Tricycioquinazolines and Molecular Orientations in Carcinogenesis", J. Chem. SOC. (C), 2641-2647 (1970).

Wolff, M.E., "Burger's Medicinal Chemistry and Drug Discovery," 5th ed., vol. 1: Principles and Practice, 975-977 (1995).

Cohen, P. et al., "The renaissance of GSK3," Nat. Rev. Mol. Biol., 2, 769-776 (2001).

Eldar-Finkelman, H. et al., "Challenges and opportunities with glycogen synthase kinase-3 inhibitors for insulin resistance and Type 2 diabetes treatment," Expert Opinion on Investigational Drugs, 12(9): 1511-1519 (2003).

Harrington, E.A. et al., "VX-680, a potent and selective small-molecule inhibitor of the Aurora kinases, suppresses tumor growth in vivo," Nat. Med., 10(3): 262-267 (2004).

Heutink, P., "Untangling tau-related dementia", Hum. Mol. Genet., 9(6): 979-986 (2000).

Nigg, E.A., "Mitotic Kinases as Regulators of Cell Division and its Checkpoints," Nat. Rev. Mol. Cell Biol., 2: 21-32 (2001).

Caplus listing Accession No. 1994:292136, Nakajima, Y. et al., "Pyrazoles agricultural and horticultural bactericides," JP 06065237 (1994).

Database CA "Online!" Chemical Abstract Service, Columbus, OH, US; Kelarev, V.I. et al., "Synthesis of amino derivatives of 1,3,5-triazine containing 1,3-4-thiadiazole fragments," Database Accession No. 1998:69514 XP002242653 abstract & Izvestiya Vysshikh Uchebnkh Zavedenii, Khimiya I Khimicheskaya Tekhnologiya, 40(5): 27-32 (1997).

Chalmers, D.T. et al., "Corticotrophin-releasing factor receptors: from molecular biology to drug design," TiPS, 17, 769-776 (2001).

Kim, L. et al., "GSK3, a master switch regulating cell-fate specification and tumorigenesis," Current Opinion in Genetics & Development, 10:508-514 (2000).

Lyrer, P., Schweiz. Med. Woohen Schr., 124(45); 2005-2012 (1994).

Banker, G.S. et al., "Modern Pharmaceutics", 451 & 596, 3rd ed., Marcel Dekker, New York (1996).

Lovestone, S. et al., "Alzheimer's disease-like phosphorylation of the microtubule-associated protein tau by glycogen synthase kinase-3 in transfected mammalian cells", Curr. Biol., 4(12), 1077-86 (1994).

Brownlees, J. et al., "Tau phosphorylation in transgenic mice expressing glycogen synthase kinase-3beta transgenes", Neuroreport., 8(15), 3251-5 (1997).

Biagi, G. et al., "Synthesis of 4,6 Disubstituted and 4,5,6-Trisubstituted-2-Phenyl-pyrimidines and Their Affinity Towards Al Adenosine Receptors", Farmaco., 52(1), 61-65 (1997).

Ali, N.M. et al, "Palladium-Catalyzed Cross Coupling Reactions of Arylboronic Acids with Pi-Deficient Heteroaryl Chlorides" Tetrahedron, 48 (37), 8117-8126 (1992).

Zhang, Z. et al., "Destabilization of β catenin by mutations in presenilin-1 potentiates neuronal apoptosis", Nature, 395, 698-702 (1998).

Takashima, K. et al., "Tau Protein Kinase I is Essential for Amyloid α-Protein-Induced Neurotoxicity", PNAS 90, 7789-7793 (1993).

Pei, J. et al., "Distribution, Levels, and Activity of Glycogen Synthase Kinase-3 in the Alzheimer Disease Brain", J. Neuropathol. Exp., 56, 70-78 (1997).

IUPAC Compendium of Chemical Terminology on a definition of "aliphatic compounds" found from http://www.chemsoc.org/chembytes/goldbook/index.htm (last visited on Nov. 18, 2007).

Glossary of Class Names of Organic Compounds and Reactive Intermediates Based on Structure found from http://www.chem.qmul.ac.uk/iupac/class/index.html (last visited on Nov. 18, 2007).

Nomenclature found from http://www.cem.msu.edu/~reusch/VirtualText/nomen1.htm (last visited on Nov. 18, 2007).

Coghlan, M.P. et al., "Selective small molecule inhibitors of glycogen synthase kinase-3 modulate glycogen metabolism and gene transcription", Chemistry & Biology, 7, 793-83 (2000).

Klein, P.S. et al., "A molecular mechanism for the effect of lithium on development", PNAS, 93: 8455-8459 (1996).

Cross, D.A.E. et al., "The inhibition of glycogen synthase kinase-3 by insulin or insulin-like growth factor 1 in the rat skeletal muscle cell line L6 is blocked by wortmannin, but not by rapamycin: evidence that wortmannin blocks activation of the mitogen-activated protein kinase pathway in L6 cells between Ras and Raf", Biochem J., 303: 21-26 (1994).

Massillon, D. et al., "Identification of the glycogenic compound 5-iodotubercidin as a general protein kinase inhibitor", Biochem J., 299: 123-128 (1994).

Fox T. et al., "A single amino acid substitution makes ERK2 susceptible to pyridinyl imidazole inhibitors of p38 MAP kinase", Protein Sci., 7: 2249-2255 (1998).

Takayanagi, H. et al., "Suppression of arthritic bone destruction by adenovirus-mediated csk gene transfer to synoviocytes and osteoclasts", J. Clin. Invest., 104, 137-146 (1999).

Boschelli et al., "Small molecule inhibitors of Src family kinases", Drugs of the Future, 25(7): 717-736 (2000).

Talamonti, M.S. et al., "Increase in activity and level of pp60c-src in progressive stages of human colorectal cancer", J Clin Invest., 91(1): 53-60 (1993).

Lutz, M.L. et al., "Overexpression and Activation of the Tyrosine Kinase Src in Human Pancreatic Carcimona", Biochem. Biophys. Res. 243, 503-508 (1998).

Rosen, N. et al., "Analysis of pp60c-src Protein Kinase Activity in Human Tumor Cell Lines and Tissues", J.Biol. Chem., 261, 13754-13759 (1986).

Bolen, J.B. et al., "Activation of pp60c-src protein kinase activity in human colon carcinoma", PNAS, 84, 2251-2255 (1987).

Masaki, T. et al., "pp60c-src Activation in Hepatocellular Carcinoma of Humans and LEC Rats", Hapatology, 27, 1257 (1998).

Biscardi, J.S. et al., "c-Src, Receptor Tyrosine Kinases, and Human Cancer", Adv. Cancer Res., 76, 61 (1999).

Lynch, S.A. et al., "Increased Expression of the src Proto-Oncogene in Hairy Cell Leukemia and a Subgroup of B-Cell Lymphomas", Leukemia, 7(9), 1416-1422 (1993).

Wiener, J.R., "Decreased Src Tyrosine Kinase Activity Inhibits Malignant Human Ovarian Cancer Tumor Growth in a Nude Mouse Model", Clin. Cancer Res., 5, 2164-2170 (1999).

Staley, C.A. et al., "Decreased Tumorigenicity of a Human Colon Adenocarcinoma Cell Line by an Antisense Expression Vector Specific for c-Src", Cell Growth Diff., 8, 269-274 (1997).

Singhal, N. et al., "Synthesis and Antimalarial Activity of Some New Quinazoline Derivatives", Indian Chem. Soc., 61, 690-693 (1984).

Kim, Y.Z. et al., "Synthesis and Antimicrobial Activity of Novel [(3-Aminopyrimidiniumyl)thio]methyl Cephalosporins", J. Med. Chem., 37(22); 3828-3833 (1994).

Rueeger, H et al., "Design, synthesis and SAR of a series of 2-substituted 4-amino-quinazoline neuropeptide Y Y5 receptor antagonists", Bioorg. Med. Chem. Lett., 10(11), 1175-1180 (2000).

Gershon, H. et al., "Pyrimidines. 7. A Study of the Chlorination of Pyrimidines with Phosphorus Oxychloride in the Presence of N,N-Dimethylaniline", J. Heterocyclic Chem., 21, 1161-1167 (1984).

Ife, R. J. et al., "Reversible Inhibitors of the Gastric (H+/K+)-ATPase. 5. Substituted 2,4-Diaminoquinazolines and Thienopyrimidines", J. Med. Chem., 38(14); 2763-2773 (1995).

Tanzi, K. et al., "Purines. X. Reactivities of Methyl Groups on 9-Phenylpurines : Condensation with an Aldehyde or an Ester, and Oxidation with Selenium Dioxide", Chem. Phar. Bull., 40 (1), 227-229 (1992).

Haq, S. et al., "Glycogen Synthase Kinase-3β Is a Negative Regulator of Cardiomyocyte Hypertrophy", J. Cell Biol., 151(1), 117-129 (2000).

Fischer, P.M. et al., "Inhibitors of Cyclin-Dependent Kinases as Anti-Cancer Therapeutics", Current Med. Chem., 7, 1213-1245 (2000).

Mani, S. et al., "Cyclin-dependent kinase: novel anticancer agents", Exp. Opin. Invest. Drugs., 8, 1849-1870 (2000).

Fry, D.W. et al., "Inhibitors of cyclin-dependent kinases as therapeutic agents for the treatment of cancer", Current Opin. Oncol. Endoc. & Metab. Investig., 2-40-59 (2000).

Bokemeyer, D. et al., "Multiple intracellular MAP kinase signaling cascades", Kidney Int., 49, 1187-1198 (1996).

Anderson, N. G. et al., "Multiple intracellular MAP kinase signaling cascades", Nature, 343, 651-653 (1990).

Crews, C.M. et al., "The Primary Structure of MEK, a Protein Kinase That Phosphorylates the ERK Gene Product", Science, 258, 478-480 (1992).

Bjorbaek, C. et al, "Divergent Functional Roles for p90rsk Kinase Domains", J. Biol. Chem., 270(32), 18848-18552 (1995).

Rouse, J. et al., A Novel Kinase Cascade Triggered by Stress and Heat Shock That Stimulates MAPKAP Kinase-2 and Phosphorylation of the Small Heat Shock Proteins, Cell, 78, 1027-1037 (1994).

Raingeaud, J. et al., MMK3- and MMK6-Regulated Gene Expression Is Mediated by p38 Mitogen-Activated Protein Kinase Signal Transduction Pathway, Mol. Cell. Biol., 16, 1247-1255 (1996).

Chen, R.H. et al., "Phosphorylation of the c-Fos transrepression domain by mitogen-activated protein kinase and 90-kDa ribosomal S6 kinase", Proc. Natl. Acad. Sci. USA, 90, 10952-10956 (1993).

Moodie, S.A. et al., "Complexes of Ras-GTP with Raf-1 and Mitogen-Activated Protein Kinase Kinase", Science, 260 (5114), 1658-1661 (1993).

Frey, R.S. et al., "Involvement of Extracellular Signal-regulated Kinase 2 and Stress-activated Protein Kinase/Jun N-Terminal Kinase Activation by Transforming Growth Factor β in the Negative Growth Control of Breast Cancer Cells", Cancer Res., 57, 628-633 (1997).

Sivaraman, V.S., et al., "Hyperexpression of Mitogen-activated Protein Kinase in Human Breast Cancer", J. Clin. Invest., 99(7), 1478-1483 (1997).

Whelchel, A. et al., "Inhibition of ERK Activation Attenuates Endothelin-stimulated Airway Smooth Muscle Cell Proliferation", Am. J. Respir. Cell Mol. Biol., 16, 589-596 (1997).

Yuan, Z.Q. et al., "Frequent activation of AKT2 and induction of apoptosis by inhibition of phosphoinositide-3-OH kinase/Akt pathway in human ovarian cancer", Oncogene, 19, 2324-2330 (2000).

Kazuhiko, N. et al., "Akt/Protein Kinase B Prevents Injury-Induced Motoneuron Death and Accelerates Axonal Regeneration", J. of Neuroscience, 20(8), 2875-2986 (2000).

Molina, T.J. et al., "Profound block in thymocyte development in mice lacking p56lck", Nature, 357, 161-164 (1992).

Kimura, M. et al., "Cell Cycle-dependent Expression and Centrosome Localization of a Third Human Aurora/Ipl1-related Protein Kinase, AIK3", J. Biol. Chem., 274(11), 13766-13771 (1997).

Namikawa, Kazuhiko et al., "Akt/Protein Kinase B Prevents Injury-Induced Motoneuron Death and Accelerates Axonal Regeneration." The Journal of Neuroscience, 20(8), 2875-2886 (2000).

Duhe, et al. "Negative regulation of janus kinases", Cell Biochem. Biophys., 341(1):17-59, (2001).

Rane, et al. "Janus kinaeses: components of multiple signaling pathways", Oncogene, 19(49):5662-56679, (2000).

Kim et al., "GSK3, a master switch regulating cell-fate specification and tumorignesis", Curr. Opin. Genet. Dev., 10(5):508-514, (2000).

* cited by examiner

*p<0.05 compared to vehicle control (two-tailed Student's t-test)

COMPOSITIONS USEFUL AS INHIBITORS OF GSK-3

CROSS REFERENCE TO RELATED APPLICATIONS

This application is a divisional of U.S. patent application Ser. No. 10/632,340, filed Aug. 1, 2003; now U.S. Pat. No. 7,491,730, which claims the benefit of U.S. Provisional Patent Application No. 60/400,967 filed Aug. 2, 2002, the contents of which are incorporated herein by reference.

TECHNICAL FIELD OF INVENTION

The present invention relates to inhibitors of protein kinases, especially glycogen synthase kinase-3 (GSK-3), a serine/threonine protein kinase. The invention also provides compositions comprising the inhibitors of the invention and methods utilizing those compositions in the treatment of various disorders, such as diabetes, Alzheimer's disease, Huntington's disease, Parkinson's disease, multiple sclerosis (MS), stroke, neurological and neurodegenerative disorders, and psychiatric disorders.

BACKGROUND OF THE INVENTION

The search for new therapeutic agents has been greatly aided in recent years by a better understanding of the structure of enzymes and other biomolecules associated with target diseases. One important class of enzymes that has been the subject of extensive study is protein kinases.

Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g., osmotic shock, heat shock, ultraviolet radiation, bacterial endotoxin, and H2O2), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents.

Glycogen synthase kinase-3 (GSK-3) is a serine/threonine protein kinase comprised of α and β isoforms that are each encoded by distinct genes [Coghlan et al., *Chemistry & Biology*, 7, 793-803 (2000); Kim and Kimmel, *Curr. Opinion Genetics Dev.*, 10, 508-514 (2000)]. GSK-3 has been implicated in various diseases including diabetes, Alzheimer's disease, CNS disorders such as manic depressive disorder and neurodegenerative diseases, and cardiomyocyte hypertrophy [see, e.g., WO 99/65897; WO 00/38675; Kaytor and Orr, *Curr. Opin. Neurobiol.*, 12, 275-8 (2000); Haq et al., *J. Cell Biol.*, 151, 117-30 (2000); Eldar-Finkelman, *Trends Mol. Med.*, 8, 126-32 (2002)]. These diseases are associated with the abnormal operation of certain cell signaling pathways in which GSK-3 plays a role.

GSK-3 has been found to phosphorylate and modulate the activity of a number of regulatory proteins. These include glycogen synthase, which is the rate-limiting enzyme required for glycogen synthesis, the microtubule-associated protein Tau, the gene transcription factor β-catenin, the translation initiation factor e1F-2B, as well as ATP citrate lyase, axin, heat shock factor-1, c-Jun, c-myc, c-myb, CREB, and CEPBα. These diverse targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. GSK-3 is a negative regulator of the insulin-induced signal in this pathway. Normally, the presence of insulin causes inhibition of GSK-3-mediated phosphorylation and deactivation of glycogen synthase. The inhibition of GSK-3 leads to increased glycogen synthesis and glucose uptake [Klein et al., *PNAS*, 93, 8455-9 (1996); Cross et al., *Biochem. J.*, 303, 21-26 (1994); Cohen, *Biochem. Soc. Trans.*, 21, 555-567 (1993); and Massillon et al., *Biochem J.* 299, 123-128 (1994); Cohen and Frame, *Nat. Rev. Mol Cell Biol.*, 2, 769-76 (2001)]. However, where the insulin response is impaired in a diabetic patient, glycogen synthesis and glucose uptake fail to increase despite the presence of relatively high blood levels of insulin. This leads to abnormally high blood levels of glucose with acute and chronic effects that may ultimately result in cardiovascular disease, renal failure and blindness. In such patients, the normal insulin-induced inhibition of GSK-3 fails to occur. It has also been reported that GSK-3 is overexpressed in patients with type II diabetes [WO 00/38675]. Therapeutic inhibitors of GSK-3 are therefore useful for treating diabetic patients suffering from an impaired response to insulin.

Apoptosis has been implicated in the pathophysiology of ischemic brain damage (Li et al., 1997; Choi, et al., 1996; Charriaut-Marlangue et al., 1998; Grahm and Chen, 2001; Murphy et al., 1999; Nicotera et al., 1999). Recent publications indicate that activation of GSK-3β may be involved in apoptotic mechanisms (Kaytor and Orr, 2002; Culbert et al., 2001). Studies in rat models of ischemic stroke induced by middle cerebral artery occlusion (MCAO) showed increased GSK-3β expression is following ischemia (Wang et al., Brain Res, 859, 381-5, 2000; Sasaki et al., Neurol Res, 23, 588-92, 2001). Fibroblast growth factor (FGF) reduced ischemic brain injury after permanent middle cerebral artery occlusion (MCO) in rats (Fisher et al. 1995; Song et al. 2002). Indeed, the neuroprotective effects of FGF demonstrated in ischemia models in rats may be mediated by a PI-3 kinase/AKT-dependent inactivation of GSK-3β (Hashimoto et al., 2002). Thus, inhibition of GSK-3β after a cerebral ischemic event may ameliorate ischemic brain damage.

GSK-3 is also implicated in mycardial infarction. See Jonassen et al., Circ Res, 89:1191, 2001 (The reduction in myocardial infarction by insulin administration at reperfusion is mediated via Akt dependent signaling pathway); Matsui et al., Circulation, 104:330, 2001 (Akt activation preserves cardiac function and prevents cardiomyocyte injury after transient cardiac ischemia in vivo); Miao et al., J Mol Cell Cardiol, 32:2397, 2000 (Intracoronary, adenovirus-mediated Akt gene delivery in heart reduced gross infarct size following ischemia-reperfusion injury in vivo); and Fujio et al., Circulation et al., 101:660, 2000 (Akt signaling inhibits cardiac myocyte apoptosis in vitro and protects against ischemia-reperfusion injury in mouse heart).

GSK-3 activity plays a role in head trauma. See Noshita et al., Neurobiol Dis, 9:294, 2002 (Upregulation of Akt/PI3-kinase pathway may be crucial for cell survival after traumatic brain injury) and Dietrich et al., J Neurotrauma, 13:309, 1996 (Posttraumatic administration of bFGF significantly reduced damaged cortical neurons & total contusion volume in a rat model of traumatic brain injury).

GSK-3 is also known to play a role in psychiatric disorders. See Eldar-Finkelman, Trends Mol Med, 8:126, 2002; Li et al., Bipolar Disord, 4:137, 2002 (LiCl and Valproic acid, antipsychotic, mood stabilizing drugs, decrease GSK3 activities and increase beta-catenin) and Lijam et al., Cell, 90:895, 1997 (Dishevelled KO mice showed abnormal social behavior and defective sensorimotor gating. Dishevelled, a cytoplamic protein involved in WNT pathway, inhibits GSK3beta activities).

It has been shown that GSK3 inhibition by lithium and valproic acid induces axonal remodeling and change synaptic connectivity. See Kaytor & Orr, Curr Opin Neurobiol, 12:275, 2002 (Downregulation of GSK3 causes changes in microtubule-associated proteins: tau, MAP1 & 2) and Hall et al., Mol Cell Neurosci, 20:257, 2002 (Lithium and valproic acid induces the formation of growth cone-like structures along the axons).

GSK-3 activity is also associated with Alzheimer's disease. This disease is characterized by the presence of the well-known β-amyloid peptide and the formation of intracellular neurofibrillary tangles. The neurofibrillary tangles contain hyperphosphorylated Tau protein, in which Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Curr. Biol.*, 4, 1077-86 (1994); and Brownlees et al., *Neuroreport* 8, 3251-55 (1997); Kaytor and Orr, *Curr. Opin. Neurobiol.*, 12, 275-8 (2000)]. In transgenic mice overexpressing GSK3, significant increased Tau hyperphosphorylation and abnormal morphology of neurons were observed [Lucas et al., EMBO J, 20:27-39 (2001)]. Active GSK3 accumulates in cytoplasm of pretangled neurons, which can lead to neurofibrillary tangles in brains of patients with AD [Pei et al., *J Neuropathol Exp Neurol*, 58, 1010-19 (1999)]. Therefore, inhibition of GSK-3 slows or halts the generation of neurofibrillary tangles and thus treat or reduce the severity of Alzheimer's disease.

Evidence for the role GSK-3 plays in Alzheimer's disease has been shown in vitro. See Aplin et al (1996), J Neurochem 67:699; Sun et al (2002), Neurosci Lett 321:61 (GSK3b phosphorylates cytoplasmic domain of Amyloid Precursor Protein (APP) and GSK3b inhibition reduces Ab40 & Ab42 secretion in APP-transfected cells); Takashima et al (1998), PNAS 95:9637; Kirschenbaum et al (2001), J Biol Chem 276:7366 (GSK3b complexes with and phosphorylates presenilin-1, which is associated with gamma-secretase activity in the synthesis of Aβ from APP); Takashima et al (1998), Neurosci Res 31:317 (Activation of GSK3b by Ab(25-35) enhances phosphorylation of tau in hippocampal neurons. This observation provides a link between Aβ and neurofibrillary tangles composed of hyperphosphorylated tau, another pathological hallmark of AD); Takashima et al (1993), PNAS 90:7789 (Blockade of GSK3b expression or activity prevents Ab-induced neuro-degeneration of cortical and hippocampal primary cultures); Suhara et al (2003), Neurobiol Aging. 24:437 (Intracellular Ab42 is toxic to endothelial cells by interfering with activation of Akt/GSK-3b signaling-dependent mechanism); De Ferrari et al (2003) Mol Psychiatry 8:195 (Lithium protects N2A cells & primary hippocampal neurons from Aβ fibrils-induced cytotoxicity, & reduced nuclear translocation/destabilization of b-catenin); and Pigino et al., J Neurosci, 23:4499, 2003 (The mutations in Alzheimer's presenilin 1 may deregulate and increase GSK-3 activity, which in turn, impairs axonal transport in neurons. The consequent reductions in axonal transport in affected neurons can ultimately lead to neurodegeneration).

Evidence for the role GSK-3 plays in Alzheimer's disease has been shown in vivo. See Yamaguchi et al (1996), Acta Neuropathol 92:232; Pei et al (1999), J Neuropath Exp Neurol 58:1010 (GSK3b immunoreactivity is elevated in susceptible regions of AD brains); Hernandez et al (2002), J Neurochem 83:1529 (Transgenic mice with conditional GSK3b overexpression exhibit cognitive deficits similar to those in transgenic APP mouse models of AD); De Ferrari et al (2003) Mol Psychiatry 8:195 (Chronic lithium treatment rescued neurodegeneration and behavioral impairments (Morris water maze) caused by intrahippocampal injection of Aβ fibrils.); McLaurin et al., Nature Med, 8:1263, 2002 (Immunization with Aβ in a transgenic model of AD reduces both AD-like neuropathology and the spatial memory impairments); and Phiel et al (2003) Nature 423:435 (GSK3 regulates amyloid-beta peptide production via direct inhibition of gamma secretase in AD tg mice).

Presenilin-1 and kinesin-1 are also substrates for GSK-3 and relate to another mechanism for the role GSK-3 plays in Alzheimer's disease, as was recently described by Pigino, G., et al., *Journal of Neuroscience* (23:4499, 2003). It was found that GSK3beta phosphorylates kinsesin-I light chain, which results in a release of kinesin-1 from membrane-bound organelles, leading to a reduction in fast anterograde axonal transport (Morfini et al., 2002). The authors suggest that the mutations in PSI may deregulate and increase GSK-3 activity, which in turn, impairs axonal transport in neurons. The consequent reductions in axonal transport in affected neurons ultimately leads to neurodegeneration.

GSK-3 is also associated with amyotrophic lateral sclerosis (ALS). See Williamson and Cleveland, 1999 (Axonal transport is retarded in a very early phase of ALS in mSOD1 mice); Morfini et al., 2002 (GSK3 phosphorylates kinesin light chains and inhibit anterograde axonal transport); Warita et al., Apoptosis, 6:345, 2001 (The majority of spinal motor neurons lost the immunoreactivities for both PI3-K and Akt in the early and presymptomatic stage that preceded significant loss of the neurons in this SOD1 tg animal model of ALS); and Sanchez et al., 2001 (The inhibition of PI-3K induces neurite retraction mediated by GSK3 activation).

GSK-3 activity is also linked to spinal cord and peripheral nerve injuries. It has been shown that GSK3 inhibition by lithium and valproic acid can induce axonal remodeling and change synaptic connectivity. See Kaytor & Orr, Curr Opin Neurobiol, 12:275, 2002 (Downregulation of GSK3 causes changes in microtubule-associated proteins: tau, MAP1 & 2) and Hall et al., Mol Cell Neurosci, 20:257, 2002 (Lithium and valproic acid induces the formation of growth cone-like structures along the axons). See also Grothe et al., Brain Res, 885:172, 2000 (FGF2 stimulate Schwann cell proliferation and inhibit myelination during axonal growth); Grothe and Nikkhah, 2001 (FGF-2 is up regulated in the proximal and distal nerve stumps within 5 hours after nerve crush); and Sanchez et al., 2001 (The inhibition of PI-3K induces neurite retraction mediated by GSK3 activation).

Another substrate of GSK-3 is β-catenin, which is degraded after phosphorylation by GSK-3. Reduced levels of β-catenin have been reported in schizophrenic patients and have also been associated with other diseases related to increase in neuronal cell death [Zhong et al., *Nature*, 395, 698-702 (1998); Takashima et al., *PNAS*, 90, 7789-93 (1993); Pei et al., *J. Neuropathol. Exp*, 56, 70-78 (1997); and Smith et al., *Bio-org. Med. Chem.* 11, 635-639 (2001)]. Furthermore, β-catenin and Tcf-4 play a dual role in vascular remodeling by inhibiting vascular smooth muscle cell apoptosis and promoting proliferation (Wang et al., *Circ Res*, 90:340, 2002). Accordingly, GSK-3 is associated with angiogenic disorders. See also Liu et al., FASEB J, 16:950, 2002 (Activation of GSK3 reduces hepatocyte growth factor, leading to altered endothelial cell barrier function and diminished vascular integrity) and Kim et al., J Biol Chem, 277:41888, 2002 (GSK3beta activation inhibits angiogenesis in vivo using Matrigel plug assay: the inhibition of GSK3beta signaling enhances capillary formation).

Association between GSK-3 and Huntington's disease has been shown. See Carmichael et al., J Biol Chem., 277:33791, 2002 (GSK3beta inhibition protect cells from polyglutamine-induced neuronal and non-neuronal cell death via increases in b-catenin and its associated transcriptional pathway). Overexpression of GSK3 reduced the activation of heat shock transcription factor-1 and heat shock protein HSP70 (Bijur et al., J Biol Chem, 275:7583, 2000) that are shown to decrease both poly-(Q) aggregates and cell death in in vitro HD model (Wyttenbach et al., Hum Mol Genet, 11:1137, 2002).

GSK-3 effects the levels of FGF-2 and their receptors are increased during remyelination of brain aggregate cultures remyelinating rat brains. See Copelman et al., 2000, Messersmith, et al., 2000; and Hinks and Franklin, 2000. It was also found that FGF-2 induces process outgrowth by oligodendrocytes implicating involvement of FGF in remyelination (Oh and Yong, 1996; Gogate et al., 1994) and that FGF-2 gene therapy has shown to improve the recovery of experimental allergic encephalomyelitis (EAE) mice (Ruffini, et al., 2001).

GSK-3 has also been associated with hair growth because Wnt/beta-catenin signaling is shown to play a major role in hair follicle morphogenesis and differentiation (Kishimotot et al. Genes Dev, 14:1181, 2000; Millar, J Invest Dermatol, 118:216, 2002). It was found that mice with constitutive overexpression of the inhibitors of Wnt signaling in skin failed to develop hair follicles. Wnt signals are required for the initial development of hair follicles and GSK3 constitutively regulates Wnt pathways by inhibiting beta-catenin. (Andl et al., Dev Cell 2:643, 2002). A transient Wnt signal provides the crucial initial stimulus for the start of a new hair growth cycle, by activating beta-catenin and TCF-regulated gene transcription in epithelial hair follicle precursors (Van Mater et al., Genes Dev, 17:1219, 2003)

Because GSK-3 activity is associated with sperm motility, GSK-3 inhibition is useful as a male contraceptive. It was shown that a decline in sperm GSK3 activity is associated with sperm motility development in bovine and monkey epididymis (Vijayaraghavan et al., Biol Reprod, 54: 709, 1996; Smith et al., J Androl, 20:47, 1999). Furthermore, tyrosine & serine/threonine phosphorylation of GSK3 is high in motile compared to immotile sperm in bulls (Vijayaraghavan et al., Biol Reprod, 62:1647, 2000). This effect was also demonstrated with human sperm (Luconi et al., Human Reprod, 16:1931, 2001).

Considering the lack of currently available treatment options for the majority of the conditions associated with GSK-3 protein kinase, there is still a great need for new therapeutic agents that inhibit this protein target.

SUMMARY OF THE INVENTION

The present invention addresses this need by providing compounds of formula I:

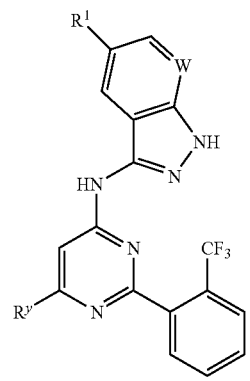

or a pharmaceutically acceptable salt thereof, wherein W, $R^1$, and $R^y$ are as described below.

The compounds of this invention are capable of inhibiting GSK-3 activity. According to the invention, these compounds are also utilized in compositions and methods for inhibiting GSK-3 activity and methods for treating or lessening the severity of diseases or conditions associated with GSK-3 in patients.

The diseases or conditions amenable to the methods of this invention include, for example, neurological and neurodegenerative disorders, diabetes, psychiatric disorders, multiple sclerosis (MS), myocardial infarction, reperfusion/ischemia, baldness, and stroke.

DETAILED DESCRIPTION OF THE INVENTION

Figure 1:
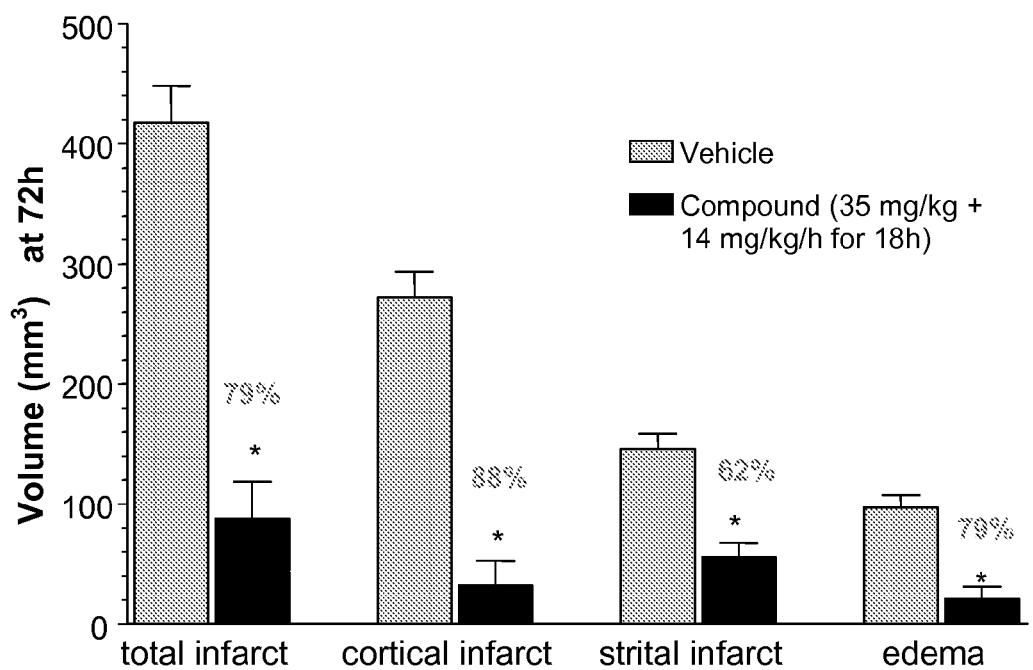
FIG. 1 depicts effects of treatment with a compound of formula I as compared to vehicle control, administered 6 hours after the Middle Cerebral Artery Occlusion Model (MCAO), as a decrease in total infarct volume, cortical infarct volume, striatal ischemic damage, and edema formation.

The present invention provides a compound of formula I:

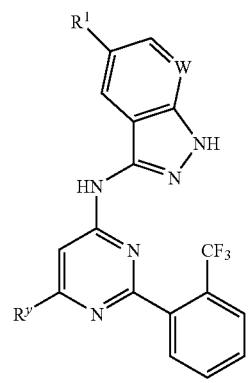

or a pharmaceutically acceptable salt thereof, wherein:

W is nitrogen or CH;

$R^1$ is selected from hydrogen or fluorine; and $R^y$ is a $C_{1-4}$ aliphatic group, optionally substituted with $N(R^2)_2$ or a 5-6 membered saturated ring having 1-2 heteroatoms independently selected from nitrogen, oxygen, or sulfur, wherein:

each $R^2$ is independently selected from hydrogen or a $C_{1-3}$ aliphatic group optionally substituted with OH, $N(R^3)_2$, or a 5-6 membered saturated ring having 1-2 heteroatoms independently selected from nitrogen, oxygen, or sulfur; and wherein:

each $R^3$ is independently selected from hydrogen or a $C_{1-3}$ aliphatic group;

provided that:

when $R^1$ is hydrogen and W is CH, then $R^y$ is other than methyl.

The term "aliphatic" or "aliphatic group" as used herein means a straight-chain or branched $C_1$-$C_4$ hydrocarbon chain that is completely saturated or that contains one or more units of unsaturation, or a monocyclic $C_3$-$C_4$ hydrocarbon that is completely saturated or that contains one or more units of unsaturation, but which is not aromatic (also referred to herein as "carbocycle" or "cycloalkyl"), that has a single point of attachment to the rest of the molecule. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl", "alkenyl" and "alkynyl" used alone or as part of a larger moiety shall include both straight and branched chains containing one to four carbon atoms and at least two carbon atoms and one double bond in the case of alkenyl and at least two carbon atoms and one triple bond, in the case of alkynyl.

The compounds utilized in this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Compounds of the present invention fall within the genus of compounds described in PCT publication WO 02/22607. However, applicants have discovered that the present compounds have surprising and unexpectedly increased potency in the protection of neuronal cells against ischemic injury and the treatment of stroke.

One aspect of the present invention relates to a compound of formula I wherein $R^y$ is an unsubstituted $C_{1-4}$ aliphatic group. Preferred aliphatic groups of compounds of formula I are alkyl groups. Such alkyl groups are preferably methyl, ethyl, cyclopropyl, tert-butyl, or isopropyl. More preferred alkyl groups of formula I are methyl, cyclopropyl, and tert-butyl.

According to one embodiment, the present invention relates to a compound of formula I wherein $R^y$ is a $C_{1-4}$ aliphatic group substituted with a 6-membered saturated ring having 1-2 heteroatoms independently selected from nitrogen, oxygen, or sulfur. Such 6-membered saturated rings include morpholinyl, piperidinyl, and piperazinyl.

According to another embodiment, the present invention relates to a compound of formula I wherein $R^y$ is a $C_{1-4}$ aliphatic group substituted with $N(R^2)_2$.

In certain embodiments, the present invention relates to a compound of formula I wherein $R^2$ is hydrogen.

According to another embodiment, the present invention relates to a compound of formula I wherein $R^2$ is an unsubstituted $C_{1-3}$ aliphatic group.

Yet another embodiment relates to a compound of formula I wherein $R^2$ is a $C_{1-3}$ aliphatic group substituted with OH or $N(R^3)_2$.

Yet another embodiment relates to a compound of formula I wherein $R^2$ is a $C_{1-3}$ aliphatic group substituted with a 6-membered saturated ring having 1-2 heteroatoms independently selected from nitrogen, oxygen, or sulfur. Such 6-membered saturated rings include morpholinyl, piperidinyl, and piperazinyl.

According to one embodiment, the present invention relates to a compound of formula I wherein W is nitrogen.

According to another embodiment, the present invention relates to a compound of formula I wherein W is CH.

According to yet another embodiment, the present invention relates to a compound of formula I wherein $R^1$ is hydrogen.

According to another embodiment, the present invention relates to a compound of formula I wherein $R^1$ is fluorine.

It is understood that all combinations and subcombinations of embodiments, as described herein, are within the scope of the present invention.

Representative examples of compounds of formula I are set forth in Table 1 below.

TABLE 1

Compounds of Formula I

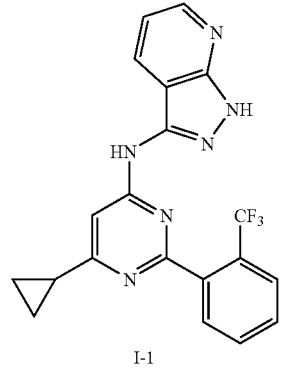

I-1

TABLE 1-continued

Compounds of Formula I

I-2

I-3

I-4

I-5

I-6

I-7

I-8

I-9

TABLE 1-continued

Compounds of Formula I

I-10

I-11

I-12

I-13

I-14

I-15

I-16

I-17

TABLE 1-continued

Compounds of Formula I

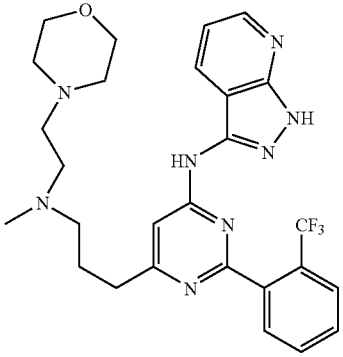

I-18

The compounds of this invention may be prepared as illustrated by the Schemes I-II below and by general methods known to those skilled in the art.

Scheme I above shows a general method for preparing compounds of the present invention. At step (a), the aryl amide 1 is treated with oxalyl chloride to form the acyl isocyanate 2. As shown at step (c), an acyl isocyanate 2 may be condensed with an enamine 3 to provide pyrimidinone 4 (J. Org. Chem. (1993), 58, 414-418; J. Med. Chem., (1992), 35, 1515-1520; J. Org. Chem., 91967, 32, 313-214). Intermediate 4 is treated with $POCl_3$ to form the chloro compound 5 which is then combined with the amino-indazole derivative 6 to provide a compound of formula I. Methods for preparing the amino-indazole derivatives 6 are known in the art. Specifically, the synthesis of these derivatives are set forth in WO 02/22607.

Scheme II

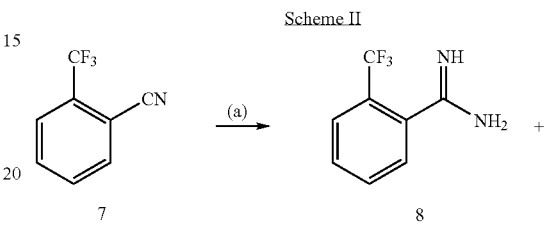

Scheme 1

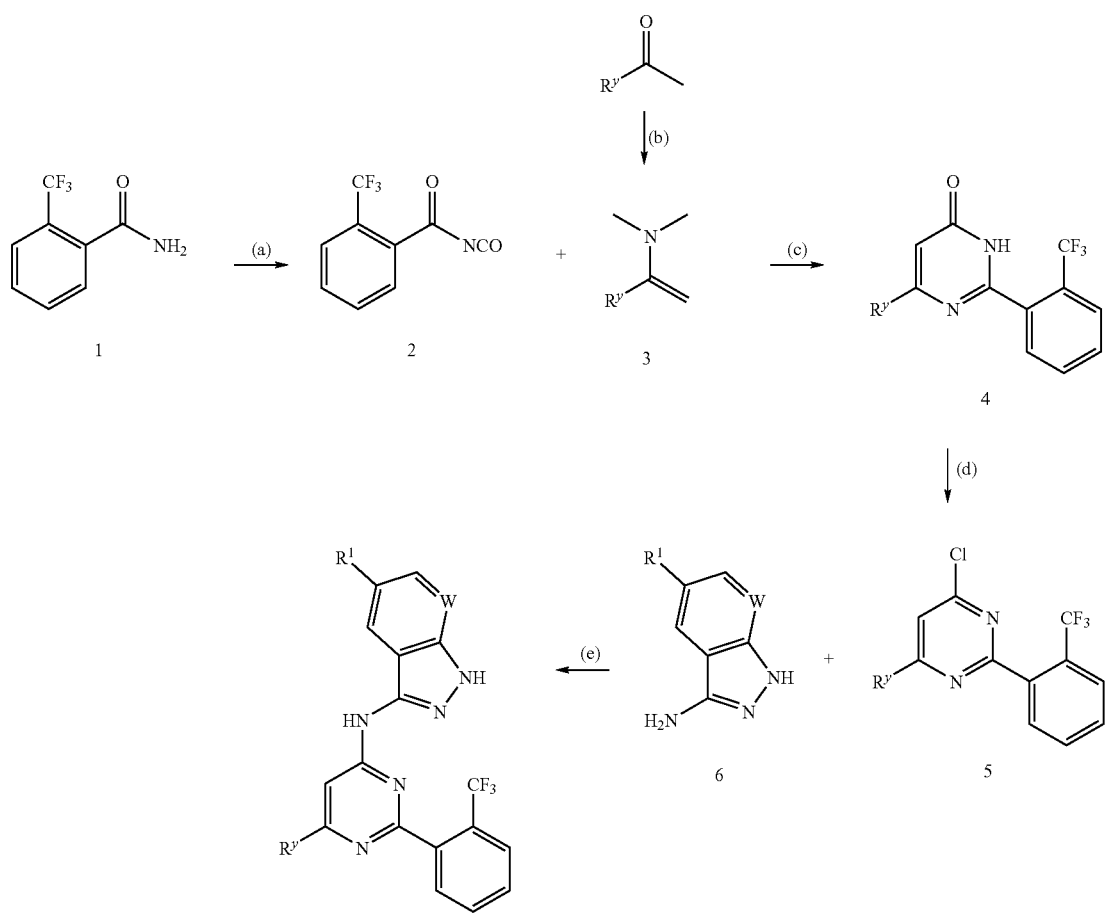

Reagents and conditions: (a) oxalyl chloride, dichloroethane, 70° C.; (b) dimethylamine, pentane, $TiCl_4$; (c) $NH_4OAc$, HOAc, THF, reflux; (d) $POCl_3$, n-$Pr_3N$, reflux; (e) 160° C., neat.

-continued

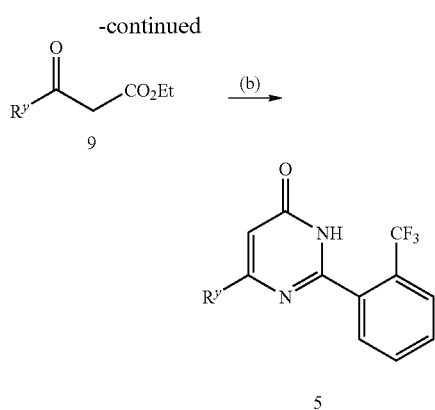

Reagents and conditions: (a) i LiN(TMS)₂, ether, THF, ii HCl; (b) NaOEt, EtOH, reflux.

Scheme II above shows an alternative method for preparing pyrimidinone intermediate 5, which may be utilized in the preparation of compounds of formula I as depicted in Scheme I at step (e) above. At step (a), the aryl nitrile 7 is benzamidine intermediate 8 is then treated with the beta-keto ester 9 to form the pyrimidinone compound 5 which may be utilized as described above.

One having ordinary skill in the art may synthesize other compounds of this invention following the teachings of the specification using reagents that are readily synthesized or commercially available.

The activity of a compound utilized in this invention as an inhibitor of GSK-3 may be assayed in vitro, in vivo or in a cell line. In vitro assays include assays that determine inhibition of either the phosphorylation activity or ATPase activity of activated GSK-3. Alternate in vitro assays quantitate the ability of the inhibitor to bind to GSK-3. Inhibitor binding may be measured by radiolabelling the inhibitor prior to binding, isolating the inhibitor/GSK-3 complex and determining the amount of radiolabel bound. Alternatively, inhibitor binding may be determined by running a competition experiment where new inhibitors are incubated with GSK-3 bound to known radioligands.

According to another embodiment, the invention provides a composition comprising a compound of this invention or a pharmaceutically acceptable salt thereof and a pharmaceutically acceptable carrier, adjuvant, or vehicle. The amount of compound in the compositions of this invention is such that is effective to detectably inhibit a protein kinase, particularly GSK-3, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in GSK-3 activity between a sample comprising said composition and GSK-3 kinase and an equivalent sample comprising GSK-3 kinase in the absence of said composition.

A "pharmaceutically acceptable salt" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite of a compound of the present invention, or residue thereof, is also an inhibitor of GSK-3 kinase.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention.

For example, neurotrophic factors or other agents for treating neurological or neurodegenerative disorders may be combined with the compounds of this invention to treat neurological and neurodegenerative disorders. Examples of known neurotrophic factors include, but are not limited to, acetylcholinesterase inhibitors, MAO inhibitors, interferons, anti-convulsants, ion channel blockers, riluzole, and anti-Parkinsonian agents.

Examples of known treatments for stroke include Activase®, a recombinant, or genetically engineered, tissue plasminogen activator (rt-PA), heparin, glutamate antagonists, calcium antagonists, opiate antagonists, GABA agonists and antioxidants.

Other examples of agents the compounds of this invention may also be combined with include, without limitation, anti-depressive agents, such as Zoloft®, Prozac®, Paxil®, and Buspar®; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating diabetes such as insulin, insulin analogues, alpha glucosidase inhibitors, biguanides, and insulin sensitizers; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the present invention relates to administering to a patient an additional therapeutic agent selected from a treatment for Alzheimer's Disease (AD), a treatment for Parkinson's Disease, an agent for treating Multiple Sclerosis (MS), a treatment for asthma, an anti-inflammatory agent, an immunomodulatory or immunosuppressive agent, a neurotrophic factor, an agent for treating stroke, an agent for treating cardiovascular disease, an anti-depressant, an anti-psychotic agent, or an agent for treating diabetes, wherein:

said additional therapeutic agent is appropriate for the disease being treated; and said additional therapeutic agent is administered together with said composition as a single dosage form or separately from said composition as part of a multiple dosage form.

According to another embodiment, the invention relates to a method of inhibiting GSK-3 kinase activity in a biological sample comprising the step of contacting said biological sample with a compound of this invention, or composition comprising said compound.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition of GSK-3 kinase activity in a biological sample is useful for a variety of purposes which are known to one of skill in the art. Examples of such purposes include, but are not limited to, blood transfusion, organ-transplantation, biological specimen storage, and biological assays.

According to another embodiment, the invention relates to a method of inhibiting GSK-3 kinase activity in a patient comprising the step of administering to said patient a compound of this invention, or composition comprising said compound.

According to another embodiment, the invention provides a method for treating or lessening the severity of a GSK-3-mediated disease or condition in a patient comprising the step of administering to said patient a composition according to the present invention.

The term "GSK-3-mediated disease" as used herein, means any disease or other deleterious condition or disease in which GSK-3 is known to play a role. Such diseases or conditions include, without limitation, autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease.

According to another embodiment, the present invention relates to a method for treating or lessening the severity of a disease, disorder, or condition selected from an autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease, in a patient in need thereof, comprising administering to said patient a compound of the present invention or composition thereof.

According to another embodiment, the present invention relates to a method for treating or lessening the severity of a disease or condition selected from allergy, asthma, diabetes, Alzheimer's disease, Huntington's disease, Parkinson's disease, AIDS-associated dementia, amyotrophic lateral sclerosis (ALS, Lou Gehrig's disease), multiple sclerosis (MS), an injury due to head trauma, schizophrenia, anxiety, bipolar disorder, tauopothy, a spinal cord or peripheral nerve injury, myocardial infarction, cardiomyocyte hypertrophy, glaucoma, attention deficit disorder (ADD), depression, a sleep disorder, reperfusion/ischemia, stroke, an angiogenic disorder, or baldness, wherein said method comprises administering to a patient in need thereof a compound of the present invention or composition thereof.

According to a preferred embodiment, the method of the present invention relates to treating or lessening the severity of stroke.

According to another preferred embodiment, the method of the present invention relates to treating or lessening the severity of a neurodegenerative or neurological disorder.

Another aspect of the present invention relates to a method of decreasing sperm motility in a male patient comprising administering to said patient a compound of the present invention or composition thereof.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

In order that the invention described herein may be more fully understood, the following examples are set forth. It should be understood that these examples are for illustrative purposes only and are not to be construed as limiting this invention in any manner.

EXAMPLES

As used herein, the HPLC Method designated as "Method A" is as follows:

Column: C18, 3 um, 2.1×50 mm, "Lighting" by Jones Chromatography.

Gradient: 100% water (containing 1% acetonitrile, 0.1% TFA) to 100% acetonitrile (containing 0.1% TFA) over 4.0 minutes, hold at 100% acetonitrile for 1.4 minutes and return to initial conditions.

Total run time 7.0 minutes.

Flow rate: 0.8 mL/minute.

As used herein, the term "$R_t$" refers to the retention time, in minutes, obtained for the compound using the designated HPLC method. Compound numbers recited in the Examples below correspond to the compound numbers recited in Table 1, supra.

Example 1

6-Methyl-2-(2-trifluoromethyl-phenyl)-3H-pyrimidin-4-one: A mixture of 2-trifluoromethyl-benzamidine (2.13 g, 4 mmol) and sodium ethoxide (0.83 g, 12 mmol) in ethanol (20 mL) was treated with methyl acetoacetate (0.44 mL, 4 mmol) and heated at for 24 hours. The reaction was cooled, concentrated, diluted with water and acidified with 2 N hydrochloric acid. The resulting solution was extracted with ethyl acetate, dried over sodium sulfate and concentrated. Purification by flash chromatography [SiO$_2$, methanol:dichloromethane (3:97)] provided the title compound (0.51 g, 50% yield) as a yellow solid; $^1$H-NMR (500 MHz, DMSO-d$_6$) δ 12.7 (br s, 1H), 7.9 (m, 1H), 7.8 (m, 2H), 7.7 (m, 1H), 6.3 (s, 1H), 2.21 (s, 3H) ppm; MS (FIA) 255.0 (M+H); R$_t$ (Method A) 2.578 minutes.

Example 2

4-Chloro-6-methyl-2-(2-trifluoromethyl-phenyl)-pyrimidine: A solution of 6-methyl-2-(2-trifluoromethyl-phenyl)-3H-pyrimidin-4-one (10.7 g, 41.9 mmol) in phosphorous oxychloride (39 mL, 419 mmol) was treated with tri-n-propylamine (16 mL, 83.9 mmol) and refluxed at 110-120° C. for 1 hours. The solvent was evaporated, azeotroped three times with toluene, then dried in vacuo. The residue was taken up in ethyl acetate, washed sequentially with 1 N sodium hydroxide, water and brine, then dried over sodium sulfate and concentrated. Purification by flash chromatography [SiO$_2$, ethyl acetate:hexanes (1:9)] provided the title compound (9.61 g, 84% yield) as an orange oil.
$^1$H NMR (CDCl$_3$, 500 MHz) δ 2.63 (3H, s), 7.26 (s, 1H), 7.61 (t, J=7.6 Hz, 1H), 7.67 (t, J=7.5 Hz, 1H), 7.76 (d, J=7.6 Hz, 1H), 7.82 (d, J=7.8 Hz, 1H) ppm; MS (FIA) 273.0 (M+H); R$_t$ (Method A) 3.499 min.

Example 3

(5-Fluoro-1H-indazol-3-yl)-[6-methyl-2-(2-trifluoromethyl-phenyl)-pyrimidin-4-yl]amine (I-2): A mixture of 4-chloro-6-methyl-2-(2-trifluoromethyl-phenyl)-pyrimidine (0.10 g, 0.37 mmol) and 5-fluoro-1H-indazole-3-ylamine (0.072 g, 0.48 mmol) was heated neat at 160-170° C. for 8 hours. The resulting residue was cooled to ambient temperature then dissolved in N-methyl-pyrrolidinone (2 mL). This mixture was poured into water (20 mL) and sodium bicarbonate (5 mL) was added and the resulting mixture filtered, washing with water. Purification by preparative HPLC provided the title compound (0.081 g, 43% yield) as a tan solid. $^1$H-NMR (500 MHz, DMSO-d$_6$) δ 12.8 (br s, 1H), 10.6 (br s, 1H), 7.86 (d, J=8.0 Hz, 1H), 7.77 (m, 4H), 7.62 (br s, 1H), 7.50 (m, 1H), 7.29 (m, 1H), 2.44 (s, 3H) ppm; LC-MS 388.05 (M+H); R$_t$ (Method A) 2.900 minutes.

Example 4

6-tert-Butyl-2-(2-trifluoromethyl-phenyl)-3H-pyrimidin-4-one: A mixture of 2-trifluoromethylbenzamidine (1.12 g, 5 mmol), sodium ethoxide (1.02 g, 15 mmol) and 4,4-dimethyl-3-oxo-pentanoic acid methyl ester (0.80 mL, 5 mmol) in ethanol (50 mL) and was heated at reflux for 16 hours. The reaction was cooled, concentrated, diluted with water and acidified with 2 N hydrochloric acid. This solution was extracted with ethyl acetate, dried over sodium sulfate and concentrated. Purification by flash chromatography [SiO$_2$, methanol:dichloromethane (2:98)] provided the title compound (0.48 g, 32% yield) as a yellow solid; $^1$H-NMR (500 MHz, DMSO-d$_6$) δ 12.8 (br s, 1H), 7.89 (d, J=7.5 Hz, 1H), 7.78 (m, 2H), 7.71 (d, J=7.4 Hz, 1H), 6.24 (s, 1H), 1.20 (s, 9H) ppm; LC-MS 297.03 (M+H); R$_t$ (Method A) 3.30 minutes.

Example 5

6-tert-Butyl-6-chloro-2-(2-trifluoromethyl-phenyl)-pyrimidine: A solution of 6-tert-butyl-2-(2-trifluoromethyl-phenyl)-3H-pyrimidin-4-one (0.47 g, 1.59 mmol) in phosphorous oxychloride (1.65 mL, 15.9 mmol) was treated with tri-n-propylamine (0.61 mL, 3.17 mmol) and heated at 110-120° C. for 1 hour. The solvent was removed by evaporation then azeotroped three times with toluene. The residue was taken up in ethyl acetate, washed sequentially with 1 N sodium hydroxide, water and brine, then dried over sodium sulfate and concentrated. Purification by flash chromatography [SiO$_2$, ethyl acetate:hexanes (1:9)] provided the title compound (0.33 g, 66% yield) as a yellow oil.
$^1$H NMR (CDCl$_3$, 500 MHz) δ 1.31 (9H, s), 7.25 (s, 1H), 7.51 (t, J=7.6 Hz, 1H), 7.58 (t, J=7.5 Hz, 1H), 7.74 (t, J=8.5 Hz, 2H) ppm; MS (FIA) 314.9 (M+H); R$_t$ (Method A) 4.156 minutes.

Example 6

[6-tert-Butyl-2-(2-trifluoromethyl-phenyl)-pyrimidin-4-yl]-(1H-pyrazolo[3,4-b]pyridin-3-yl)-amine (I-3): A mixture of 4-chloro-6-tert-butyl-2-(2-trifluoromethyl-phenyl)-pyrimidine (0.10 g, 0.32 mmol) and 1H-pyrazolo[3,4-b]pyridin-3-ylamine (0.064 g, 0.48 mmol) was heated neat at 160-170° C. for 16 hours. The resulting residue was cooled, dissolved in N-methyl-pyrrolidinone (2 mL), then poured into water (20 mL) and sodium bicarbonate (5 mL) and extracted twice with ethyl acetate. The combined organic layers were washed four times with water, once with brine, then dried over sodium sulfate and concentrated. The crude product was purified by preparative HPLC to provide the title compound (0.007 g, 4% yield) as a yellow solid. $^1$H-NMR (500 MHz, DMSO-d$_6$) δ 13.2 (br s, 1H), 10.6 (br s, 1H), 8.49 (m, 2H), 7.84 (d, J=7.8 Hz, 2H), 7.76 (m, 2H), 7.68 (m, 1H), 7.12 (m, 1H), 1.32 (s, 9H) ppm; LC-MS 413.08 (M+H); R$_t$ (Method A) 3.112 minutes.

Example 7

6-Cyclopropyl-2-(2-trifluoromethyl-phenyl)-3H-pyrimidin-4-one:

(1-Cyclopropyl-vinyl)-dimethylamine
To a solution of cyclopropyl methylketone (19.8 mL, 200 mmol) in pentane (600 mL) at 0° C. under nitrogen was added dimethylamine/tetrahydrofuran (2M, 500 mL, 1000 mmol), then a solution of titanium(IV)chloride (12.1 mL, 110 mmol) in pentane (60 mL) was added in a dropwise fashion. The reaction was stirred 0.5 hour at 0° C. then for 5 hours at room temperature. The reaction was filtered through Celite, washing with pentane and ether, concentrated in vacuo with a bath temperature of 15-20° C. then was stored overnight as an orange oil at −4° C.

2-Trifluoromethylbenzoyl isocyanate:
A solution of 2-trifluoromethylbenzamide (34.9 g, 185 mmol) in 1,2-dichloroethane (600 mL), at room temperature under nitrogen, was treated with oxalyl chloride (20.2 mL, 230 mmol) in rapid drops and the reaction stirred at 70-80° C. overnight. The solvent was removed by evaporation, and the residue was azeotroped twice with toluene.

6-Cyclopropyl-2-(2-trifluoromethyl-phenyl)-3H-pyrimidin-4-one:
To a solution of (1-cyclopropyl-vinyl)-dimethylamine in tetrahydrofuran (400 mL) at 0° C. under nitrogen was added a solution of 2-trifluoromethylbenzoyl isocyanate in tetrahydrofuran (50 mL), in a dropwise fashion. The reaction was stirred for 0.5 hour, then ammonium acetate (78 g, 1000 mmol) and acetic acid (400 mL) was added. The reaction mixture was heated at reflux for 3 hours with continuous removal of tetrahydrofuran, then cooled and poured into water (1.2 L). The resulting precipitate was collected by filtration, washing with water and ether to provide 6-cyclopropyl-2-(2-trifluoromethyl-phenyl)-3H-pyrimidin-4-one (28.79 g, 56% yield) as a white solid which is a mixture of the title compound and (2-trifluoromethyl-benzoyl)-urea (91:9 by HPLC).
$^1$H-NMR (500 MHz, DMSO-d$_6$) δ 12.7 (br s, 1H), 7.87 (d, J=7.6 Hz, 1H), 7.79 (m, 2H), 7.73 (d, J=7.5 Hz, 1H), 6.32 (s, 1H), 1.93 (m, 1H), 0.90 (m, 4H), [urea: 10.8 (br s, 1H), 7.45 (br s, 1H)] ppm; LC-MS 280.96 (M+H); R$_t$ (Method A) 2.961 minutes (title compound), 2.313 minutes (urea impurity).

Example 8

4-Chloro-6-cyclopropyl-2-(2-trifluoromethyl-phenyl)-pyrimidine: 6-Cyclopropyl-2-(2-trifluoromethyl-phenyl)-3H-pyrimidin-4-one (12.0 g, 42.8 mmol) in phosphorous oxychloride (40 mL, 428 mmol) was heated at 75-80° C. for 1 hour. The solvent was removed by evaporation and azeotroping three times with toluene. The residue was cooled to 0° C., taken up in ethyl acetate, treated with ice chips and water. The mixture was then washed sequentially with sodium bicarbonate, water and brine, dried over sodium sulfate and concentrated. Purification by flash chromatography [SiO$_2$, 5:95 ethyl acetate:hexanes (5:95)] provided the title compound (9.71 g, 76% yield) as a colorless oil. $^1$H NMR (CDCl$_3$, 500 MHz) δ 1.12 (m, 2H), 1.30 (m, 2H). 2.02 (m, 1H), 7.24 (s, 1H), 7.56 (t, J=7.6 Hz, 1H), 7.64 (t, J=7.6 Hz, 1H), 7.79 (m, 2H) ppm; MS (FIA) 299.1/300.9 (M+H); R$_t$ (Method A) 3.882 minutes.

Example 9

[6-Cyclopropyl-2-(2-trifluoromethyl-phenyl)-pyrimidin-4-yl]-(1H-indazol-3-yl)-amine (I-4): A mixture of 4-chloro-6-cyclopropyl-2-(2-trifluoromethyl-phenyl)-pyrimidine (0.08 g, 0.27 mmol) and 1H-indazol-3-ylamine (0.036 g, 0.41 mmol) was heated neat at 160-170° C. for 6 hours. The residue was cooled and dissolved in N-methyl-pyrrolidinone (2 mL), poured into water (30 mL) and sodium bicarbonate (5 mL) then filtered, washing with water and ether. The collected precipitate and the ether wash were combined and concentrated. Purification by flash chromatography [SiO$_2$, methanol:dichloromethane (2:98)] provided the title compound (0.017 g, 15% yield) as a pale yellow solid. $^1$H-NMR (500 MHz, DMSO-d$_6$) δ 12.6 (br s, 1H), 10.2 (br s, 1H), 8.00 (d, J=8.1 Hz, 2H), 7.81 (d, J=7.9 Hz, 1H), 7.71 (m, 3H), 7.65 (t, J=7.3 Hz, 1H), 7.45 (d, J=8.4 Hz, 1H), 7.36 (t, J=7.5 Hz, 1H), 7.06 (t, J=7.5 Hz, 1H), 2.04 (m, 1H), 1.01 (m, 2H), 0.96 (m, 2H) ppm; LC-MS 396.10 (M+H); R$_t$ (Method A) 3.122 minutes.

Example 10

[6-Cyclopropyl-2-(2-trifluoromethyl-phenyl)-pyrimidin-4-yl]-(1H-pyrazolo[3,4-b]pyridin-3-yl)-amine (I-1): A mixture of 4-chloro-6-cyclopropyl-2-(2-trifluoromethyl-phenyl)-pyrimidine (7.00 g, 23.4 mmol, prepared as described above in example 8) and 1H-pyrazolo[3,4-b]pyridin-3-ylamine (9.43 g, 70.3 mmol) in N-methylpyrrolidinone (50 mL) was heated at 130° C. for 12 hours. The residue was cooled, dissolved in N-methyl-pyrrolidinone (2 mL), poured into water (500 mL) and sodium bicarbonate (15 mL) then filtered, washing with water. Purification by flash chromatography [SiO$_2$, ethyl acetate:hexanes (35:65)] provided the title compound (5.25 g, 57% yield) as a white solid. $^1$H-NMR (500 MHz, DMSO-d$_6$) δ 13.1 (br s, 1H), 10.5 (br s, 1H), 8.50 (m, 2H), 7.82 (d, J=7.8 Hz, 1H), 7.73 (m, 3H), 7.66 (t, J=7.7 Hz, 1H), 7.12 (m, 1H), 2.07 (m, 1H), 1.02 (m, 2H), 0.97 (m, 2H) ppm; LC-MS 397.22 (M+H); R$_t$ (Method A) 3.412 minutes.

Example 11

[6-Cyclopropyl-2-(2-trifluoromethyl-phenyl)-pyrimidin-4-yl]-(1H-pyrazolo[3,4-b]pyridin-3-yl)-amine, hydrochloride salt: The HCl salt was prepared by dissolving compound I-1 (8.42 g, 21.4 mmol) in 6N hydrochloric acid and lyophilizing to provide the title compound (9.242 g, 99%) as a yellow solid. $^1$H-NMR (500 MHz, DMSO-d$_6$) δ 13.3 (br s, 1H), 10.9 (br s, 1H), 8.53 (dd, J=4.4, 1.4 Hz, 1H), 8.48 (br d, J=7.4 Hz, 1H), 7.87 (d, J=7.8 Hz, 1H), 7.79 (m, 2H), 7.72 (t, J=6.8 Hz, 2H), 7.15 (m, 1H), 2.14 (m, 1H), 1.07 (m, 4H) ppm; MS (FIA) 397.3 (M+H), 395.2 (M–H), 431.2 (M–H+HCl); R$_t$ (Method A) 2.798 minutes.

Example 12

6-But-3-enyl-2-(2-trifluoromethyl-phenyl)-3H-pyrimidin-4-one: 6-But-3-enyl-2-(2-trifluoromethyl-phenyl)-3H-pyrimidin-4-one was prepared as described above in Example 1, except using 3-oxo-hept-6-enoic acid ethyl ester. The reaction provided the title compound (2.545 g, 49% yield) as a cream-colored solid. $^1$H-NMR (500 MHz, DMSO-d6) δ 12.8 (s, 1H), 7.88 (d, 1H), 7.79 (t, 1H), 7.75 (t, 1H), 7.68 (d, 1H), 6.22 (s, 1H), 5.80 (m, 1H), 5.03 (dd, 1H), 4.98 (dd, 1H), 2.56 (t, 2H), 2.36 (m, 2H) ppm; MS (FIA) 295.1 (M+H); R$_t$ (Method A) 3.160 minutes.

Example 13

4-But-3-enyl-6-chloro-2-(2-trifluoromethyl-phenyl)-pyrimidine: The title compound was prepared as described in Example 2, except using 6-but-3-enyl-2-(2-trifluoromethyl-phenyl)-3H-pyrimidin-4-one to provide a yellow oil (0.49 g, 99% yield). $^1$H-NMR (500 MHz, DMSO-d6) δ 7.72 (d, 1H), 7.67 (d, 1H), 7.57 (t, 1H), 7.51 (t, 1H), 7.13 (s, 1H), 5.77 (m, 1H), 4.98 (m, 2H), 2.84 (t, 2H), 2.49 (m, 2H) ppm; MS (FIA) 313.0(M+H); R$_t$ (Method A) 4.220 minutes.

Example 14

[6-But-3-enyl-2-(2-trifluoromethyl-phenyl)-pyrimidin-4-yl]-(1H-pyrazolo[3,4-b]pyridin-3-yl)-amine (I-7): The title compound was prepared as described in example 6, except using 4-but-3-enyl-6-chloro-2-(2-trifluoromethyl-phenyl)-pyrimidine to provide a cream-colored solid (2.712 g, 62% yield). $^1$H-NMR (500 MHz, DMSO-d6) δ 13.1 (s, 1H), 10.56 (s, 1H), 8.50 (m, 1H), 8.47 (d, 1H), 7.84 (d, 1H), 7.76 (t, 1H), 7.69 (m, 3H), 7.13 (m, 1H), 5.86 (m, 1H), 5.06 (dd, 1H), 4.98 (dd, 1H), 2.76 (t, 2H), 2.46 (m, 2H) ppm;
MS (FIA) 411.2(M+H); Rt (Method A) 3.019 minutes.

Example 15

[6-(3-Morpholin-4-yl-propyl)-2-(2-trifluoromethyl-phenyl)pyrimidin-4-yl](1H-pyrazolo[3,4-b]pyridin-3-yl)-amine (I-8): A solution of [6-but-3-enyl-2-(2-trifluoromethyl-phenyl)-pyrimidin-4-yl]-(1H-pyrazolo[3,4-b]pyridin-3-yl)-amine (0.10 g, 0.25 mmol) in methanol (5 mL) and tetrahydrofuran (5 mL) at –78° C. was bubbled through with ozone for 5 minutes. To this mixture was added morpholine (0.05 mL, 0.56 mmol) and sodium triacetoxyborohydride (0.39 g, 1.85 mmol). The reaction was stirred at room temperature for 24 hours when additional morpholine (0.10 mL, 1.28 mmol) and sodium triacetoxyborohydride (0.39 g, 1.85 mmol) were added then the stirring continued another 2 hours. The reaction was quenched with sodium bicarbonate and evaporated. Purification by flash chromatography (SiO$_2$, eluted with 1:9 methanol:dichloromethane), followed by preparative HPLC provided the title compound as a bright yellow lyophilate (0.068 g, 38% yield). 484.3 (M+H). $^1$H-NMR (500 MHz, DMSO-d6) δ 13.2 (s, 1H), 10.7 (s, 1H), 9.60 (br s, 1H), 8.52 (m, 1H), 8.47 (d, 1H), 7.86 (d, 1H), 7.77 (m, 1H), 7.70 (m, 2H), 7.14 (m, 1H), 3.97 (br m, 2H), 3.61 (br m, 2H), 3.44 (br m, 2H), 3.18 (br m, 2H), 3.05 (br m, 2H), 2.78 (t, 2H), 2.08 (m, 2H) ppm.

Example 16

The following compounds were prepared by methods substantially similar to those described herein at Examples 1-15, the General Schemes, and by methods known to one of ordinary skill in the art.

[6-(3-Piperidin-1-yl-propyl)-2-(2-trifluoromethyl-phenyl)pyrimidin-4-yl]-(1H-pyrazolo[3,4-b]pyridin-3-yl)-amine (I-9): 482.2 (M+H). $^1$H-NMR (500 MHz, DMSO-d6) δ 13.2 (s, 1H), 10.7 (S, 1H), 9.04 (br s, 1H), 8.52 (m, 1H), 8.47 (d, 1H), 7.85 (d, 1H), 7.78 (m, 1H), 7.70 (m, 2H), 7.14 (m, 1H), 3.42 (m, 2H), 3.10 (m, 2H), 2.85 (m, 2H), 2.77 (t, 2H), 2.09 (m, 2H), 1.79 (m, 2H), 1.61 (m, 3H), 1.35 (m, 1H) ppm.

[6-(3-Diethylamino-propyl)-2-(2-trifluoromethyl-phenyl)pyrimidin-4-yl]-(1H-pyrazolo[3,4-b]pyridin-3-yl)-amine (I-10): 470 (M+H). $^1$H-NMR (500 MHz, DMSO-d6) δ 13.2 (s, 1H), 10.7 (s, 1H), 9.07 (s, 1H), 8.50 (m, 1H), 7.85 (m, 1H), 7.78 (d, 1H), 7.76 (m, 1H), 7.71 (m, 2H), 7.14 (m, 1H), 3.11 (m, 6H), 2.80 (t, 2H), 2.05 (m, 2H), 1.15 (t, 6H) ppm.

[6-(3-(4-Methyl-piperazin-1-yl)-propyl)-2-(2-trifluoromethyl-phenyl)pyrimidin-4-yl]-(1H-pyrazolo[3,4-b]pyridin-3-yl)-amine (I-11): 497.2 (M+H). $^1$H-NMR (500 MHz, DMSO-d6) δ 13.2 (s, 1H), 10.7 (s, 1H), 8.52 (m, 1H), 8.47 (m, 2H), 7.85 (d, 1H), 7.77 (m, 1H), 7.72 (m, 3H), 7.14 (m, 1H), 3.0-3.7 (br, 10H), 2.83 (s, 3H), 2.77 (t, 2H), 2.05 (m, 2H) ppm.

[6-(3-piperazin-1-yl-propyl)-2-(2-trifluoromethyl-phenyl)pyrimidin-4-yl]-(1H-pyrazolo[3,4-b]pyridin-3-yl)-amine (I-12): 483.3 (M+H). $^1$H-NMR (500 MHz, DMSO-d6) δ 13.2 (s, 1H), 10.7 (s, 1H), 9.06 (br s, 2H), 8.52 (m, 1H), 8.47 (d, 1H), 7.85 (d, 1H), 7.77 (m, 1H), 7.70 (m, 2H), 7.14 (m, 1H), 3.34 (br m, 8H), 3.15 (br m, 2H), 2.77 (t, 2H), 2.06 (m, 2H) ppm.

[6-(3-Dimethylamino-propyl)-2-(2-trifluoromethyl-phenyl)pyrimidin-4-yl]-(1H-pyrazolo[3,4-b]pyridin-3-yl)-amine (I-13): 442.1 (M+H). $^1$H-NMR (500 MHz, DMSO-d6) δ 13.2 (s, 1H), 10.7 (s, 1H), 9.40 (br s, 1H), 8.52 (m, 1H), 8.47 (d, 1H), 7.85 (d, 1H), 7.78 (m, 1H), 7.71 (m, 2H), 7.14 (m, 1H), 3.12 (m, 2H), 2.77 (m, 8H), 2.06 (m, 2H) ppm.

N,N-Dimethyl-N'-{3-[6-(1H-pyrazolo[3,4-b]pyridin-3-yl-amino)-2-(2-trifluoromethyl-phenyl)-pyrimidin-4-yl]-propyl}-ethane-1,2-diamine (I-14): 485.3 (M+H). $^1$H-NMR (500 MHz, DMSO-d6) δ 13.2 (s, 1H), 10.7 (s, 1H), 9.7 (br, 1H), 8.8 (br s, 1H), 8.52 (m, 1H), 8.48 (d, 1H), 7.85 (d, 1H), 7.77 (m, 1H), 7.71 (m, 2H) 7.14 (m, 1H), 3.32 (s, 4H), 3.07 (br m, 2H), 2.84 (s, 6H), 2.80 (m, 2H), 2.04 (m, 2H) ppm.

[6-(3-Methylamino-propyl)-2-(2-trifluoromethyl-phenyl)pyrimidin-4-yl]-(1H-pyrazolo[3,4-b]pyridin-3-yl)-amine (I-15): 428.1 (M+H). $^1$H-NMR (500 MHz, DMSO-d6) δ 13.2 (s, 1H), 10.7 (s, 1H), 8.51 (m, 1H), 8.48 (d, 1H), 8.37 (br s, 2H), 7.85 (d, 1H), 7.77 (m, 1H), 7.70 (m, 2H), 7.14 (m, 1H), 2.97 (m, 2H), 2.78 (t, 2H), 2.55 (m, 3H), 2.01 (m, 2H) ppm.

2-{3-[6-(1H-Pyrazolo[3,4-b]pyridin-3-ylamino)-2-(2-trifluoromethyl-phenyl)-pyrimidin-yl]propylamino}-ethanol (I-16): 458.2 (M+H). $^1$H-NMR (500 MHz, DMSO-d6) δ 13.2 (s, 1H), 10.7 (s, 1H), 8.52 (m, 1H), 8.47 (m, 2H), 7.85 (d, 1H), 7.77 (m, 1H), 7.69 (m, 2H), 7.14 (m, 1H), 3.62 (t, 2H), 2.99 (m, 4H), 2.78 (t, 2H), 2.04 (m, 2H) ppm.

[6-(3-(2-Morpholin-4-yl-ethylamino)-propyl)-2-(2-trifluoromethyl-phenyl)pyrimidin-4-yl]-(1H-pyrazolo[3,4-b]pyridin-3-yl)-amine (I-17): 527.2 (M+H). $^1$H-NMR (500 MHz, DMSO-d6) δ 13.2 (s, 1H), 10.7 (s, 1H), 8.76 (br s, 2H), 8.52 (m, 1H), 8.48 (d, 1H), 7.85 (d, 1H), 7.78 (m, 1H), 7.70 (m, 2H), 7.14 (m, 1H), 3.81 (br s, 4H), 3.1-3.3 (br m, 8H), 3.06 (t, 2H), 2.80 (t, 2H), 2.05 (t, 2H) ppm.

[6-{3-[Methyl-(2-morpholin-4-yl-ethyl)-amino]-propyl}-2-(2-trifluoromethyl-phenyl)pyrimidin-4-yl]-(1H-pyrazolo[3,4-b]pyridin-3-yl)-amine (I-18): 541.2 (M+H).

$^1$H-NMR (500 MHz, DMSO-d6) δ 13.2 (s, 1H), 10.7 (s, 1H), 8.52 (m, 1H), 8.47 (d, 1H), 7.85 (d, 1H), 7.78 (m, 1H), 7.70 (m, 2H), 7.14 (m, 1H), 3.73 (br s, 4H), 3.39 (m, 2H), 3.21 (m, 2H), 2.8-3.3 (br m, 6H) 2.81 (s, 3H), 2.78 (t, 2H), 2.09 (m, 2H) ppm.

Example 17

K$_i$ Determination for the Inhibition of GSK-3

Compounds were screened for their ability to inhibit GSK-3β (AA 1-420) activity using a standard coupled enzyme system (Fox et al. (1998) *Protein Sci.* 7, 2249). Reactions were carried out in a solution containing 100 mM HEPES (pH 7.5), 10 mM MgCl$_2$, 25 mM NaCl, 300 μM NADH, 1 mM DTT and 1.5% DMSO. Final substrate concentrations in the assay were 20 μM ATP (Sigma Chemicals, St Louis, Mo.) and 300 μM peptide (HSSPHQS(PO$_3$H$_2$)EDEEE, American Peptide, Sunnyvale, Calif.). Reactions were carried out at 30° C. and 20 nM GSK-3β. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of interest. The assay stock buffer solution (175 μl) was incubated in a 96 well plate with 5 μl of the test compound of interest at final concentrations spanning 0.002 μM to 30 μM at 30° C. for 10 minutes. Typically, a 12-point titration was conducted by preparing serial dilutions (from 10 mM compound stocks) with DMSO of the test compounds in daughter plates. The reaction was initiated by the addition of 20 μl of ATP (final concentration 20 μM). Rates of reaction were obtained using a Molecular Devices Spectramax plate reader (Sunnyvale, Calif.) over 10 minutes at 30° C. The K$_i$ values were determined from the rate data as a function of inhibitor concentration.

Compounds of the present invention were found to have a K$_i$ value of less than 100 nM using the above-described assay.

Example 18

Determination of the Percent Neuroprotection

As used herein, the term "Percent Protection" represents the percentage of neuronal cells protected against ischemic injury (OGD) and is calculated as:

% protection=(test-*OGD*)/(normal-*OGD*)*100

This protocol describes the procedure used to induce experimental ischemia by anoxia-reoxygenation in cultured hippocampal neuronal cells. The neuroprotective effect of test compounds is evaluated against ischemic-induced neuronal cell injury and cell death.

The following steps were performed prior to the day of the assay:

The LoG-Neurobasal [LoG-Neurobasal contains NoG-Neurobasal medium (Invitrogen Corp, customized order) plus 0.5 mM glucose, 0.5 mM L-glutamine and 0.25× Penicillin/Streptomycin] was pre-equilibrated in the hypoxic chamber overnight.

The LoG-Neurobasal was pre-equilibrated in the normal incubator (5% $CO_2$) overnight.

In the normal incubator (5% $CO_2$), Neurobasal/B27AO [Neurobasal/B27AO contains Neurobasal medium (Invitrogen Corp Cat # 21103-049) with 2× B27 minus AO supplement (Invitrogen Corp Cat #10889-038), 0.5 mM L-glutamine, and 0.25× Penicillin/Streptomycin] was pre-equilibrated overnight.

The following steps were performed the day of the assay:

LoG-Neurobasal medium was removed from the hypoxic chamber, and the medium was lightly bubbled with 100% $N_2$ for 30 minutes to deoxygenate completely.

The Neurobasal/B27m culture medium [Neurobasal/B27m contains Neurobasal medium with 2× B27 supplement (Invitrogen Corp Cat #17504-044) and 0.5 mM L-glutamine] was aspirated from the cells in each 12-well plate using the vacuum pump with a sterile glass pasteur pipette attached.

The plate was washed once with 2 ml of glucose free-$BSS_0$ (pH 7.4), prepared from the following: 143.6 mM NaCl, 5.4 mM KCl, 1.8 mM $CaCl_2$, 0.8 mM $MgSO_4$, 1 mM $NaH_2PO_4$, 26.2 mM $NaHCO_3$, 10 mg/l phenol red, and 0.25× P/S.

The neurons (10-11 days from initial culture) were replenished with deoxygenated LoG-Neurobasal (1 ml per well for each well of a 12-well plate). These neuronal cells were prepared according to Park L C, Calingasan N Y, Uchida K, Zhang H, Gibson G E. (2000) "Metabolic impairment elicits brain cell type-selective changes in oxidative stress and cell death in culture." *J Neurochem* 74(1):114-124.

The test compounds were added directly to each well (3 concentrations of the compound plus positive control, each in triplicate). The compounds were dissolved in 100% DMSO, where the concentration of DMSO never exceeded 0.5% then the plates were placed in the Hypoxic Chamber for 5 hours with the plate lids ajar.

For normoxia controls, pre-equalibrated normoxic LoG-Neurobasal medium was added to each well and the plate replaced in the normal culture incubator for 4 hours.

After 4 hours of hypoxia, the existing media was carefully aspirated off and 2 mL of new oxygenated (pre-equilibrated) Neurobasal/B27AO was added to each well. Reoxygenated medium was achieved by placing medium overnight in the culture incubator (5% $CO_2$/95% $O_2$) prior to use.

The same test compounds with same the concentrations were added back into the corresponding wells and the plates placed in the cell culture incubator (5% $CO_2$/95% $O_2$) and reoxygenated for 20-24 hours. After reoxygenation for 20-24 hours, the number of live neurons are counted using the cell tracker green fluorescence method described below.

The existing culture medium was apirated from each well of the 12 well plates and the neurons were washed once with 2 ml of HBSS (pH 7.4, Invitrogen Corp, Cat #14170-112) prewarmed to 30-37° C.

To each well of the plate was added 1 ml of 2.5 µM Cell Tracker Green ((Molecular Probes Cat # 2925) and 5 µM Hoechst 33342 fluorescent dyes dissolved in HBSS. The plates were then placed in the dark at room temperature for 15 minutes then the neurons were washed once with 2 ml of HBSS. 1 ml of HBSS was added to each well, and the numbers of live and dead fluorescent cells were counted using Cellomics® automated imaging system.

Compounds of the present invention were found to have a % protection value of >30%.

Example 19

Middle Cerebral Artery Occlusion Model (MCAO)

The animals used in this study were male Sprague-Dawley rats weighing between 270 and 333 g (Charles River, N.C.). The rats were allowed to acclimate to the animal facilities for at least one week on a 12-hour light/dark diurnal cycle. They were allowed free access to food and water.

The intraluminal arterial occluders used to block the origin of the middle cerebral artery (MCA) were made from 4-0 nylon monofilament suture cut to 25 mm long segments. The tip of the suture was rounded by exposure to heat. To increase the effectiveness of the occluder to block the lumen of the artery, they were coated with a 1% Poly-L-lysine suspension and dried for 1 hour in an oven set at 60° C. Sutures were purchased from Ethelon, Somerville, N.J. Chemical reagents were utilized as follows:

1. 2,3,5-triphenyltetrazolium chloride, or TTC, Cat #T8877, Lot #50K1435, and PEG400, Cat # P-3265, were purchased from Sigma Chemical Co., St. Louis, Mo.
2. The phosphate buffered formalin, Cat # 245-685, was purchased from Fisher Scientific Co., Middletown, Va.
3. The distilled water was produced in-house.
4. The ethanol, Cat # E702-3, was purchased from Aldridge, Milwaukee, Wis.

The intraluminal suture model of focal cerebral ischemia was used substantially as described by Longa, et al., *Stroke*, 20:84-91 (1989). The left external jugular vein was cannulated for vehicle or compound administration.

To help the rats maintain hydration during the study, 5% dextrose in water and lactated ringers solution (5 ml each) were injected subcutaneously in each flank at 10, 24, and 48 hours after MCAO.

Rats that met the initial inclusion criteria (neurological score of 2 and body temperature >38.5° C.) were randomized by sequential assignment to the vehicle or compound treatment groups. The initial daily assignment of the rats to a particular group was alternated each day.

Treatment with compound or vehicle was initiated by bolus injection i.v. 6 hours after MCAO and continued for the next 18 hours by constant infusion using the Infu Disk pump. The rats were anesthetized briefly and the jugular catheter was exposed through the dorsal neck incision. The bolus dose of compound or vehicle was administered and the infusion pump was activated 5 minutes later. The infusion pumps were attached to the back of the rats by a jacket.

Compound solutions were prepared fresh daily using a vehicle of water:PEG400:ethanol in the volume 5:4:1. The groups and the doses utilized in this model are set forth in Table 2 below.

TABLE 2

Compound Dosing for t-MCAO Model

| Group | n | Treatment | Bolus Dose* (mg/kg) | Infusion Dose (mg/kg/hr) | Bolus Compound (mg/mL) | Infusion** Compound (mg/mL) |
|---|---|---|---|---|---|---|
| 1 | 12 | Vehicle | — | — | — | — |
| 2 | 10 | Compound | 35 | 14 | 21.4 | 21.4 |

*Bolus Dose Volume of 0.49 mL
**Infusion Rate of 0.21 mL/hr and Infusion Duration of 18 hours.

The volume of infarction was determined by image analysis of 7 consecutive 2,3,5-triphenyltetrazolium chloride (TTC) stained sections using a modification of the procedure described by Bederson et al. (1986). Three days after MCAO, the rats were sacrificed by $CO_2$ asphyxiation and decapitated. The brains were quickly removed from the calvarium and placed in individual beakers containing PBS in an ice bath for 30 minutes. Coronal brain sections, 2 mm thick, were obtained using a brain matrix slicer. The brain sections were placed in labeled petri dishes containing 2% TTC in PBS for 20 minutes at 37° C. TTC stains viable brain tissue red, leaving the ischemic area white. Brain sections were then immersed in 10% neutral buffered formalin for at least 24 hours at 4° C. All the sections were imaged within 3 days of sacrifice.

Formalin fixed TTC stained brain sections (7 consecutive sections) were captured digitally using Adobe Photoshop software and a digital camera. The images were imported into IPLab image analysis program. The area of cortical infarction (white area) was outlined and measured. The infarct volume was calculated using the following formula:

Infarct volume=Σ infarct area×2 (the distance between each section)

The total ipsilateral and contralateral hemispheric volumes were determined similarly. The volume of edema was calculated by subtracting the contralateral hemispheric volume from the ipsilateral hemispheric volume. A scientist blinded to the treatment of the rats performed the analysis.

The neurological function of the rats was evaluated at 2, 24, 48 and 72 hours after MCAO using a scoring system described by Bederson et al. (1986b). The score ranged from 0 to 3 with 0 as normal and 3 indicates severe deficit.

The neurological score at 2 hours of ischemia was used as inclusion criteria into the study. If the rat did not have a neurological score of at least 2 or if he had a score of 3, he was eliminated from the study. A researcher, blinded to the treatment group of the rat, performed the neurological evaluations.

Blood samples (~0.5 mL) were obtained from the rats for pharmacokinetic analysis at 5 minutes and at 4, 22, 46 and 70 hours after the bolus injection. The rats were lightly anesthetized with isoflurane. Blood was collected in heparinized blood collection tubes (0.6 mL capacity) from a lateral tail vein using a 23-gauge butterfly infusion set. The blood samples were spun for 4 minutes (setting 10) in a microfuge. The plasma was removed, placed in labeled vials and stored at −20° C. in a freezer.

Seventy-two hours after MCAO, the rats were deeply anesthetized by $CO_2$ inhalation and as much blood as possible was obtained by cardiac puncture. The blood was put into heparinzed blood collection tubes (6 ml capacity). Plasma was separated from the blood by centrifugation at 4000 rpm for 5 minutes (Allegra R6,). The plasma was collected, placed in labeled plastic tubes and stored at −20° C. in a freezer.

Statistical analysis for the infarct size, plasma glucose, body temperature, and body weight between the vehicle and treatment groups was performed by two tailed Student's t-test. The statistical analysis of the neurological score was done by non-parametric analysis. The data are presented as mean±SEM.

Treatment with a compound of formula I, administered 6 hours after MCAO, was very effective in reducing infarct volume this model of transient focal stroke (FIG. 1). Rats in the compound treated group (88±31 mm$^3$) had a highly significant 79% reduction in total infarct volume as compare to vehicle control (418±31 mm$^3$, p<0.0001). The cortical ischemic damage in the compound treated group (32±20 mm$^3$) was also significantly reduced by 88% compared to the vehicle control (272±22 mm$^3$, p<0.0001). Treatment with a compound of formula I (55±12 mm$^3$) was able to significantly reduce striatal ischemic damage by 62% as compared to vehicle control (146±13 mm$^3$, p<0.0001). Finally, treatment with a compound of formula I (21±10 mm$^3$) reduced the amount of edema formation by 79% as compared to the vehicle control group (97±10 mm$^3$, p<0.0001).

Figure 2:
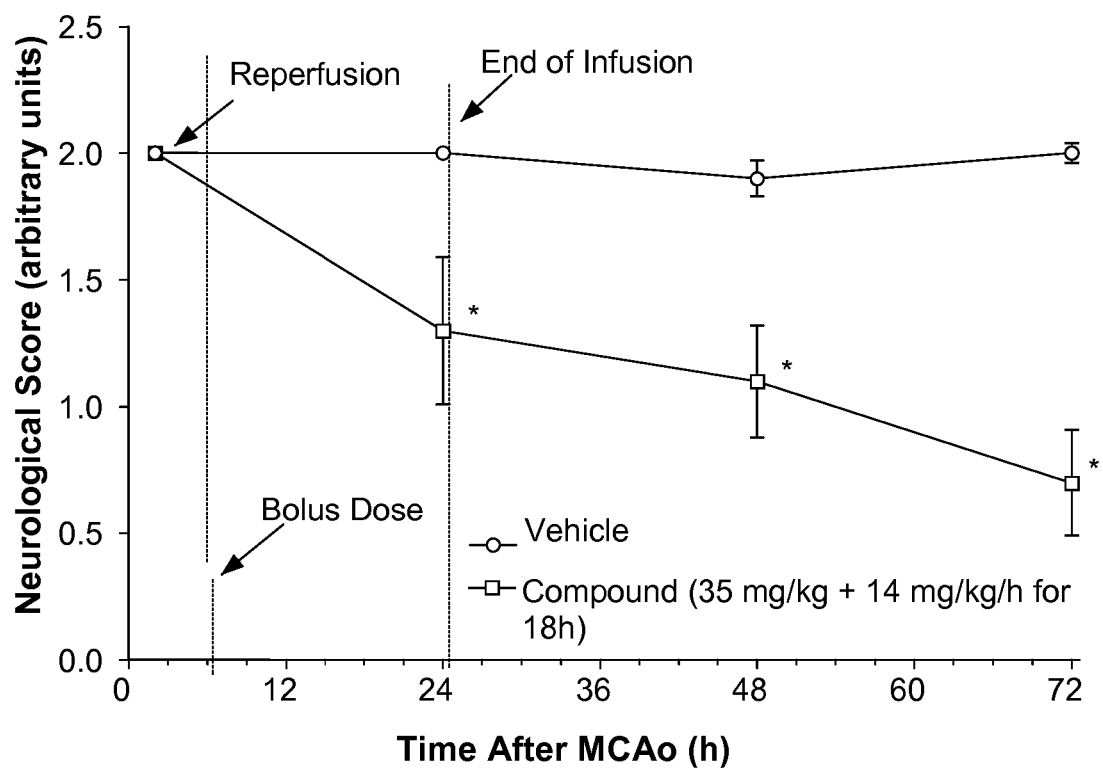
FIG. 2 depicts the neurological function of rats, over the time course of the experiment, treated with a compound of formula I as compared to the vehicle control group.

Rats treated with a compound of formula I demonstrated marked improvement in neurological function over the time course of the experiment (FIG. 2). As early as 18 hours after the initiation of dosing, a significant improvement in neurological function was observed in the compound treated group as compare to the vehicle control group (1.3±0.3 vs. 2±0 units, respectively, p<0.01). The neurological score of the rats treated with compound continued to improve so that by 72 hours after MCAO, these rats were able to function with little or no noticeable deficit. In contrast, the vehicle treated rats showed no improvement in neurological function throughout the time course of the experiment.

Example 20

Animal Model for Anti-Depressant Agent

Compounds of the present invention were assayed for anti-depressant activity in rats by methods substantially similar to those described by Porsolt, R. D., et al., 1977; 229: 327-336: Bourin M. Fundam Clin Pharmacol 1990; 4: 49-64.

Swim Test in Rats (Depression Test)

Rats are placed in a transparent cylinder filled with water. The duration of immobility (=immobility-time), defined as that time during which the rat made only those minimal body-movements to keep its head over the water, is manually recorded. In a second trial, on day 4 rats are placed again into the cylinder, this time for 5 minutes. Immobility-time is manually recorded throughout the entire trial.

Trial I (Initial Trial):

On day 1 Male Wistar rats (RA239 strain; 160-180 g) were placed for 15 minutes into a cylinder. The duration of immobility (=immobility-time), defined as that time during which the rat made only those minimal body-movements to keep its head over the water, is manually recorded. In order to test a reasonable number of animals within a day recordings are restricted to the following three sub-periods within the 15 min. trial: 0-2.5 min. (i.e. at the beginning of the trial), 6.25-8.75 minutes (exactly in the middle of the trial) and 12.5-15 minutes (at the very end of the trial). This procedure has been previously found to represent the animal's 'performance' as displayed throughout the entire trial.

Trial II (Second Trial):

On day 4 rats are placed again into the cylinder, this time for 5 minutes. Immobility-time is manually recorded throughout the entire trial.

Compound treatments were suspended in 0.5% methylcellulose (Methocel) and given orally (5 ml/kg). Drug-administrations are in the evening (around 16:00) of day 1 (the day of trial I), in the morning (around 08:00) and evening of days 2 and 3 and exactly 1 hour prior to trial II (on day 4). Treatments for the two rats within a diad were similar or different, depending on the randomization for the performance in trial I. Groups of rats treated with Methocel or 15 mg/kg p.o. Desipramine (DMI) serve as control-group and positive standard, respectively.

Compounds of the present invention were found to show anti-depressant activity in the above model.

Example 21

Animal Model of Schizophrenia: Pre-pulse Inhibition of Startle (PPI)

Impairment of sensorimotor gating linked with disruptions in attention and cognition is common among schizophrenic patients. Pre-pulse inhibition of startle (PPI) is impaired in schizophrenic patients. Pre-pulse inhibition occurs when a weak sound preceding the loud acoustic stimulus inhibits the startle reflex. PPI is considered a test with good predictive, face and construct validity for schizophrenia.

A positive control, clozapine, is a commercially-available atypical anti-psychotic drug (Clozaril®). Clozapine has a high affinity to D4 dopamine & 5-HT2 receptors and effectively enhances PPI response in animal models.

The PPI assay was performed, in the following manner, by methods substantially similar to that described by Spooren et al., Anxiolytic-like effects of the prototypical metabotropic glutamate receptor 5 antagonist 2-methyl-6-(phenylethynyl) pyridine in rodents. J Pharmacol Exp Ther. 295: 1267-1275 (2000).

Male C57BL/6 (20-30 g) were housed in groups of four in macrolon cages (42×26×15 cm) for at least 3 days before the experiment. The housing facility was temperature- and humidity-controlled and equipped with artificial illumination (6:00 AM to 6:00 PM, lights on). The animals had access to water and food, ad libitum. All animals were experimentally naïve.

Procedure animals were pretreated with test compound (30, 60, 100 mg/kg), clozapine (30 mg/kg), a positive control, or vehicle (0.5% methylcellulose). After 45 minutes, mice were individually placed in the startle chamber with a background white noise of 70 dB, and left undisturbed for 10 minutes. Then there was a 15 minute session consisting of 56 trials. The startle stimulus is a 40 ms-120 dB-white noise sound, pre-pulses are 20 ms-white noise sound of 72, 74 and 78 dB preceding the startle by 100 ms.

Eight types of trials were given: prepulse plus startle (7 trials per prepulse intensity), prepulse alone (7 trials per prepulse intensity), startle alone (7 trials), and no stimulation (7 trials). The variable intertrial interval averages 15 s (between 10 and 20 s). In the no-stimulation trials, baseline measurements were taken. In the startle alone trials, the basic auditory startle amplitude (g) was measured and in the prepulse plus startle trials, the amount of inhibition of normal startle was measured and expressed as percentage of the basic startle. In the prepulse alone trials, the normal response to a weak noise was measured as a control. Prepulse inhibition was computed according the formula, % PPI=100−100× [(PA2 PPP)/PA2]. Compounds of the present invention we found to enhance PPI of acoustic startle reflex in mice.

Example 22

Animal Models for Anxiolytic Agent

The anxiolytic assay was performed, in the following manner, by methods substantially similar to that described by Spooren et al., Anxiolytic-like effects of the prototypical metabotropic glutamate receptor 5 antagonist 2-methyl-6-(phenylethynyl)pyridine in rodents. J Pharmacol Exp Ther. 295: 1267-1275 (2000) and Lecci A, Borsini F, Volterra G and Meli A, Pharmacological validation of a novel animal model of anticipatory anxiety in mice. Psychopharmacology 101: 255-261 (1990).

I. Stress-Induced Hyperthermia:

The test procedure for stress-induced hyperthermia (SIH) was adopted with minor modification from the original description by Lecci, et al. (1990). Rectal temperature was measured to the nearest 0.1° C. by a thermometer (ELLAB instruments, Copenhagen, Denmark) via a lubricated thermistor probe (2-mm diameter) inserted 20 mm into the rectum while the mouse was hand-held near the base of the tail. The probe was left in place until steady readings were obtained (within 15 s).

Fifteen animals were housed per macrolon cage (42×26× 15 cm). At least 24 hours before the experiment animals within a cage were marked on their fur with color for later identification. Sixty minutes before taking the rectal temperature all individuals within a given cage were consecutively treated at 1-minute intervals with test compound (doses: 1.3, 10 or 30 mg/kg, p.o.; injection volume: 10 ml/kg), chlordiazepoxide-HCl (10 mg/kg, p.o.; Research Biochemicals International), i.e., the positive controls, or vehicle (0.5% methylcellulose; Animed). Exactly 30 minutes later the mice were consecutively removed from the cage (again at 1-minute intervals), and rectal temperature was determined and noted. Once temperature had been recorded, the animals were placed in a different (adjacent) cage. The dependent variable, i.e., the stress-induced hyperthermia, was defined as the delta of the median rectal temperature within the six initially removed mice and the median rectal temperature within the six last removed mice within a cage. This delta was calculated for six to eight cages depending on the specific treatment group whereas in the final representation the mean of these six to eight values was used. The rectal temperature of the very first animal was used, in addition, to evaluate the compound's potential effect on basal body temperature, per se II. Social Exploration Test in Rats:

Adult male Sprague-Dawley rats (="resident" rats; 350-400 g) and young Lister Hooded rats (="intruder" rats; 100-

120 g) were used. Intruder rats were housed in pairs and resident rats were individually housed in macrolon cages (42×26×15 cm) for 2 weeks before the test. All animals were housed in the same room. The housing facility was temperature- and humidity-controlled and equipped with artificial illumination (6:00 AM to 6:00 PM, lights on). The animals had access to water and food, ad libitum. All rats were experimentally naïve.

Animals received test compound (doses: 0.3, 3, 10 or 30 mg/kg), chlordiazepoxide-HCl (5 mg/kg, p.o.; CDZ, Research Biochemicals International, Natick, Mass.), LiCl (10, 30 mg/kg) as the reference/positive compounds, or vehicle (0.5% methylcellulose). The injection volume was 2 ml/kg. Oral treatment was given to the intruder rat only, and the test was performed 1 hour after compound administration. All observations were made during the light phase (8:00 AM to 1:00 PM) in the home cage of the resident rat (see above). The floor of the cage was covered with sawdust. Pairs consisting of one intruder rat and one resident rat were assigned at random to one of the experimental or the control groups. The duration of active approach behaviors (=time spent in social activity) of the intruder rat (sniffing, anogenital exploration, nosing, grooming, licking, playing) toward the resident was manually scored and cumulatively recorded over a period of 5 minutes.

III. Elevated Plus Maze Test:

Male adult Sprague-Dawley rats (180-220 g) were housed in groups of four in macrolon cages (42×26×15 cm) for at least 3 days before the experiment. The housing facility was temperature- and humidity-controlled and equipped with artificial illumination (6:00 AM to 6:00 PM, lights on). The animals had access to water and food, ad libitum. All animals were experimentally naïve.

The elevated plus-maze consists of two open arms (40×12 cm) and two enclosed arms (40×12×20 cm), which all extend from a common central platform (12×12 cm). The configuration forms the shape of a plus sign, with similar arms arranged opposite to each another, and the apparatus is elevated 60 cm above the floor on a central pedestal. The maze is made from gray Plexiglas. The grip on the open arms is facilitated by inclusion of a small raised edge (0.25 cm) around their perimeter.

The method was performed, in the following manner, by methods substantially similar to those described by Handley, S. L. and Mithani, S Effects of alpha-adrenoceptor agonists and antagonists in a maze exploration model of "fear"-motivated behaviour. *Naunyn-Schmiedeberg's Arch Pharmacol* 327: 1-5 (1984). Rats were randomly allocated to one of the various treatments. Animals were transported from the housing room to the laboratory at least 1 hour before testing. After oral compound administration, rats were individually housed in macrolon cages (22×16×14 cm), and after 60 minutes placed onto the central platform facing an enclosed arm. An 8-minute trial was performed, and the maze was thoroughly cleaned between subjects. Direct registrations were made by an observer sitting close to the maze, and the following conventional parameters were used: number of open and closed arm entries (arm entry defined as all four paws entering an arm) and time spent on open arms (excluding the central platform). Animals from the different treatment groups were alternatively tested, and trials were performed between 8:30 AM and 12:30 PM, i.e., within the first half of the light phase. The following anxiety reflecting parameters were recorded: ratio (open/total)time spent on open arms, latency to leave 1st arm, and total number of arm entries.

Compounds of the present invention show an anxiolytic-like effect in the above animal models.

Example 23

Cell Assay for Alzheimer's Disease—Neuronal Survival

The following assay is performed by methods substantially similar to that described by Kienlen-Campard, et al., *J Biol Chem* 277:15666 (2002). Primary cultures of hippocampal neurons are prepared from E18 rat embryos (Park et al., *J Neurochem,* 74:114, 2000). Cells are plated in 6- or 96-well culture dishes (4×10⁵ cells/cm2) or glass coverslips (1.25× 10⁵ cells/cm2) pretreated with poly(D-lysine) and cultured for 6 days in vitro in NEUROBASAL™ medium supplemented with 2% B-27 and 0.5 mM L-glutamine prior to infection with recombinant adenoviruses. Under these conditions, neuronal cultures (up to 98% of neurons) display high differentiation and survival rates.

Recombinant Adenoviruses and Neuronal Infection—Production, propagation, and purification of adenoviruses-encoding mutant form of APP695 are made. After 6 days in vitro, neuronal cultures are infected at the multiplicity of infection of 100 for 4 hours in a minimal volume of culture medium. Infection medium is then replaced by fresh culture medium for 3-5 days. Under these conditions, at least 75% of neurons express the proteins encoded by recombinant adenoviruses.

Cell Survival—Neuronal survival is measured by the calorimetric MTT assay or CellTracker fluorescent cell viability assay using Cellomics automated imaging system. For nuclear staining, cells are fixed (0.37% formaldehyde/0.2% glutaraldehyde in phosphate-buffered saline) and incubated for 30 minutes in the Hoechst 33342 dye (1 µg/ml).

Quantification of Abeta production—Culture medium is collected, treated with protease inhibitors (1 µg/ml pepstatin, 10 µg/ml leupeptin, 1 mM phenylmethylsulfonyl fluoride), and cleared by centrifugation (16,000×g, 5 min, 4° C.). One hundred µl of the supernatant is used for beta amyloid quantification using the ELISA method described below.

Example 24

Inhibition of Beta Amyloid (1-40) Production

Alzheimer's disease is characterized by the presence of extracellular plaques and intercellular neurofibrillary tangles in the brain. The major protein component of these plaques is beta amyloid ("Aβ") peptide which is cleaved from amyloid precursor protein ("APP").

Cell Line and Compound Treatment:

A stable cell line capable of secretion of Aβ was constructed in human H4 neuroglioma cells by transduction with a retroviral vector that expresses both APP695 containing the Swedish mutations (K595N, M596L) and YFP as a selection marker. Stable transductants expressing APP695 were selected by sorting cells expressing high levels of YFP.

Cells were plated at 80,000 cells per well in a 96 well plate in Dulbecco's Modified Eagle Medium (Invitrogen, catalog #11965-092) supplemented with 10% fetal bovine serum (FBS) and pencillin/streptomycin. After 24 hours, the media was replaced with fresh media containing the compound of interest where compound concentrations ranging from 20 µM to 10 nM were tested in seven-point titrations in duplicate. After incubating with test compound for 18-24 hours at 37°

C., the hAβ (1-40) concentration in the supernatant was determined using the hAβ40 ELISA.

ELISA Assay for Secreted Aβ

The Biosource International, Inc. Signal Select™ Human β Amyloid (hAβ40) ELISA (catalog #KHB3482) was used for the in vitro quantitative determination of hAβ40 in the culture supernatant of samples. A monoclonal antibody specific for the $NH_2$ terminus of hAβ was coated onto the wells of the microtiter plates. Samples, including standards of known hAβ content, were pipetted into these wells followed by the addition of a rabbit antibody specific for the 1-40 sequence of hAβ. Bound rabbit antibody was then detected by the use of a horseradish peroxidase-labeled anti-rabbit antibody. After removal of excess anti-rabbit antibody, a substrate solution was added, which was cleaved by the bound enzyme to produce color. The intensity of this colored produced is directly proportional to the concentration of hAβ (1-40) present in the sample.

The ELISA Assay was Performed as follows:

Samples and standards containing a known concentration of hAβ (1-40) peptide were diluted in standard/sample diluent (Biosource reagent). The protease inhibitors AEBSF, Aprotinin, Bestatin, E-64, Leupeptin, and Pepstatin A (Calbiochem, Protease Inhibitor Cocktail Set III, catalog #539134) were added to all samples to prevent proteolysis of the Aβpeptides. 100 µl of samples and standards were added to wells of the 96-well ELISA plates and incubated for either 2 hours at room temperature or overnight at 4° C. The wells were washed 4 times with 100 µl of wash buffer (Biosource Reagent) then 100 µl of detection antibody was then added and the plates were incubated for 2 hours at room temperature. The detection antibody recognizes the hAβ (1-40) sequence.

The wells were washed 4 times with 100 µl of wash buffer then 100 µl of horseradish peroxidase (HRP)-labeled anti-rabbit secondary antibody was added. The plates were incubated for 2 hours at room temperature. The wells were then washed 5 times with 100 µl of wash buffer then 100 µl of stabilized chromogen was added. The plates were incubated for 30 minutes at room temperature in the dark. The stabilized chromogen is a substrate solution which when cleaved by bound HRP turns blue and therefore can be monitored in a standard microtiter plate reader. 100 µl of stop solution was then added and the intensity of the color in the wells was measured at 450 nm using a Molecular Devices SpectraMAX 340 plate reader. Typically the compounds were analyzed in a 7-point dose response performed in duplicate with compound concentration ranges from 20 µM to 10 nM. Concentrations of Aβ (1-40) in the samples were calculated from standard curves generated from standards that contained a known concentration of Aβ peptide.

Compounds of the present invention were tested over a 3-day period. Each day, the Calbiochem gamma secretase "Inhibitor X" was included as a control. This is a cell-permeable hydroxyethylene dipeptide isostere with a reported IC50 of 50 nM (catalog #565771).

Example 25

Transgenic Animal Assays for Alzheimer's Disease (AD)

I. AD Transgenic Animals

Transgenic mice overexpressing the 695-amino acid isoform of human Alzheimer beta-amyloid (Abeta) precursor protein containing a Lys670-->Asn, Met671-->Leu mutation (Tg2576 mice are commercially available from Taconic, N.Y.) had normal learning and memory in spatial reference and alternation tasks at 3 months of age but showed impairment by 9 to 10 months of age. A fivefold increase in Abeta (1-40) and a 14-fold increase in Abeta(1-42/43) accompanied the appearance of these behavioral deficits. Numerous Abeta plaques that stained with Congo red dye are present in cortical and limbic structures of mice with elevated amounts of Abeta. The correlative appearance of behavioral, biochemical, and pathological abnormalities reminiscent of Alzheimer's disease in these transgenic mice suggests new opportunities for exploring the pathophysiology and neurobiology of this disease. See Correlative memory deficits, Abeta elevation, and amyloid plaques in transgenic mice. *Science* 1996 Oct. 4; 274(5284):99-102.

Although Tg2576 mice are specified in the models described herein, it would be understood that other transgenic mice, available both commercially and privately, are amenable for use in said models.

II. Beta-Amyloid ELISA Protocol

The Relationship between Aβ and Memory in the Tg2576 Mouse Model of Alzheimer's Disease. *The Journal of Neuroscience*, Mar. 1, 2002, 22(5):1858-1867.

Frozen hemibrains are sequentially extracted in a two-step extraction [sonication in (1) 2% SDS and (2) 70% formic acid (FA)]. The latter fraction is designated Abnsol. After sonication the samples are centrifuged at 100,000×g for 1 hour at 4° C., the supernatant is recovered, and the pellet is sonicated with the next solution. Brain extracts are measured by sandwich ELISA as described previously (Suzuki et al., 1994; Gravina et al., 1995). The following systems are used: (1) BAN-50 capture and BA-27 or BC-05 detection or (2) 3160 capture and BA-27 or BC-05 detection, both of which detect Aβ 1-40 and Aβ 1-42, respectively. The direct comparison of many Tg2576 brains from mice of all ages showed that the amounts of Aβ40 and Aβ42 detected with 3160 capture ELISAs are essentially the same as when BAN-50 is used for capture. The 2% SDS extracts are diluted at least 1:40 so that the assay could be performed in 0.05% SDS. Greater dilutions are corrected for SDS so that they are also assayed in 0.05% SDS. The FA extract is neutralized by a 1:20 dilution into 1 M Tris phosphate buffer, pH 8.0. The program Softmax is used to calculate femtomoles per milliliter by comparing the sample absorbance to the absorbance of known concentrations of synthetic Aβ1-40 and Aβ1-42 in identical solution as the samples, and these values are corrected with the wet weight of the original homogenate to be finally expressed as picomoles per gram wet weight. In all instances, nontransgenic tissues are processed identically in parallel with transgenic tissues.

III. Behavioral Test of Transgenic Mice: Morris Water Maze

The water maze is tailored to Tg2576 mice in the B6/SJL strain background in a manner that enabled us to detect and distinguish all stages of memory loss. This protocol provided the sensitivity, specificity, and dynamic range needed to measure changes that are subtle early in life and gross late in life. Interpolation of probes during training provided sensitivity. Adoption of exclusion criteria for performance deficits gave specificity. Training extensively lent dynamic range. The assignment of mean probe scores (MPSs), which is the mean percentage time spent by a mouse in the target quadrant during the three probe trials, improved quantification of cognitive performance of individual mice for correlations with molecular markers and provided a single measure with a broad dynamic range. Protocols for Tg2576 mice in other strain backgrounds may need to be adjusted for strain-specific differences in rates of learning and performance deficits. See The Relationship between Aβ and Memory in the Tg2576 Mouse Model of Alzheimer's Disease. *The Journal of Neuroscience*, Mar. 1, 2002, 22(5):1858-1867.

The water maze is a circular 1 or 1.2 m pool filled with water at 25-27° C. and made opaque by the addition of nontoxic white paint. The pool is placed amid fixed spatial cues consisting of boldly patterned curtains and shelves containing distinct objects. Mice are placed in a beaker and gently lowered into the water facing the wall of the pool. Mice first underwent visible platform training for 3 consecutive days (eight trials per day), swimming to a raised platform (a square surface 12×12 cm2) marked with a black and white striped pole. Visible platform days are split into two training blocks of four trials for statistical analysis. During visible platform training, both the platform location (NE, SE, SW, or NW) and start position (N, NE, E, SE, S, SW, W, or NR, excluding the positions immediately adjacent to the platform) are varied pseudorandomly in each trial. Pseudorandomization ensured that all positions are sampled before a given position is repeated. Hidden-platform training is conducted over 9 consecutive days (four trials per day), wherein mice are allowed to search for a platform submerged 1.5 cm beneath the surface of the water. Mice failing to reach the platform within 60 sec are led to the platform with a metal escape scoop. During hidden-platform trials, the location of the platform remained constant (NE, SE, SW, or NW), and mice entered the pool in one of the seven pseudorandomly selected locations (N, NE, E, SE, S, SW, W, or NR, excluding the position immediately adjacent to the platform). After each hidden platform trial, mice remained on the platform for 30 seconds and are removed from the platform and returned to their home cage with the escape scoop. Mice quickly learned to associate the scoop with escaping from the pool and consistently oriented to or followed the scoop on its appearance. The ability of mice to orient to or follow the escape scoop represented independent measures of vision and attention. At the beginning of the 4th, 7th, and 10th day of hidden platform training, a probe trial is conducted in which the platform is removed from the pool and mice are allowed to search for the platform for 60 seconds. All trials are monitored by a camera mounted directly above the pool and are recorded and analyzed using a computerized tracking system.

The MPS is calculated for each mouse and used to assess retention of spatial information in the Morris water maze. By integrating information from the intercalated probes, the MPS represents a measurement of learning similar in concept to the previously described learning index (Gallagher et al., 1993), which samples memory at different stages of learning. Similar statistical results are found with MPS, the learning index and learning score (the weighted sum of percentage time spent in the target quadrant during probe trials), and we elected to represent our data using MPS because of ease of representation.

After testing, a subset of each group of mice is euthanized, and the right hemibrain is frozen in liquid nitrogen for Aβ measurements. All brains are analyzed in a coded manner.

IV. Behavioral Test of Transgenic Mice: Exploratory Activity Anxiety and Motor Coordination See Transgenic mice expressing the betaAPP695SWE mutation: effects on exploratory activity, anxiety, and motor coordination. *Brain Res* 2003 Jul. 4; 977(1):38-45.

Spontaneous alternation is tested in a T-maze made of white acrylic. The maze consisted of a central stem (length: 30 cm) flanked on each side by two arms (length: 30 cm). The maze width is 9 cm and each wall is 20 cm in height. On the initial trial, the mice are placed in the stem of the T-maze with the right arm blocked by a plastic barrier (forced choice). After entering the available arm, the mice are kept in it for 60 seconds by closing the barrier behind them. The mice are then retrieved and after removing the barrier are immediately placed back in the stem for a free-choice trial, in which the mice could either explore the opposite arm or the same one (four-paw criterion). On the following 9 days, the same two-trial procedure is repeated, except that the blocked arm on the first trial is switched from right on odd days to left on even days. The number of alternations and the latencies before responding during the choice trial are measured, with a cut-off period of 1 minute per trial. If the mice had not responded within 1 minute and are far from the choice point, they are briefly prodded from behind, usually not more than once, so that a response could be recorded on every trial.

Motor activity is measured in the open-field, made of white acrylic with a 50×50 cm surface area and 38 cm high walls. The activity in the central and peripheral zones is recorded by an overhead video camera and analyzed. The central zone is square-shaped and began at a distance of 25 cm from each wall. The mice are placed in a corner of the open-field for three daily 5-minute sessions. The distance traveled and the time spent resting (<2 cm/s), moving slow (2-5 cm/s), or moving fast (>5 cm/s) in each zone is measured, as well as time spent in the periphery and center of the apparatus.

The elevated plus-maze consisted of four arms (length: 70 cm, width: 10 cm, height from floor: 40 cm) in a cross-shaped form and a central region (10 cm$^2$). Two of the arms are enclosed on three sides by walls (height: 10 cm) while the other two are open, except for a minimal border (height: 0.5 cm), used to minimize falls. The two enclosed or open arms faced each other. The mice are placed in the central region and the number of entries and durations in enclosed and open arms are measured for two daily 5-minute sessions with the same video-track equipment used as in the previous test. The open/total arm entries and duration ratios are then calculated. On the rare occasions when the mice fell from an open arm, the recorded time is stopped and the mice placed back at the exact position it fell from. After each session of spontaneous alternation, open-field, and plus-maze testing, the apparatus is wiped clean with a wet cloth and dried before initiation of the next trial in order to reduce the possible effects of odor cues.

The stationary beam is constructed of plastic, with a diameter of 2.5 cm and a length of 110 cm. The beam is covered by a layer of white masking tape in order to secure a firm grip and divided into 11 segments by line drawings. The beam is placed at a height of 45 cm from a mat-covered floor, which served to cushion falls and thereby prevent injury to the mice. A cardboard wall is inserted at the end of the beam to prevent the mice from escaping. A trial began by placing the mice on the middle segment. The number of segments crossed (four-paw criterion), the latencies before falling, and the number of falls are measured in a single four-trial session. The cut-off period is 1 minute per trial and the intertrial interval 15 minutes.

The accelerating rotorod (Model 7650, Stoelting, Wood Dale, Ill., USA) is constructed of ribbed plastic (diameter: 3 cm). The beam is placed at a height of 13.5 cm from floor level and separated into five sections (width: 5.5 cm) by a plastic barrier. Facing away from the experimenter's view, the mice are placed on top of the already revolving rod (4 rpm) in the orientation opposite to its movement, so that falls could be avoided by forward locomotion. The rotorod accelerated gradually and smoothly from 4 to 40 rpm during each 5-minute trial. Latencies before falling are measured for three daily sessions of four trials, with an intertrial interval of 15 minutes. Whenever the mice clung to the rod without moving (passive rotation) for two complete revolutions in succession, it is considered to have fallen. Since no mouse appeared to jump deliberately, a valid estimation of motor skills could be obtained. After training, the occurrence of various normal and pathological reflexes is evaluated.

V. Brain Beta-Amyloid Accumulation Determination by Immunohistochemistry

See Accelerated plaque accumulation, associative learning deficits, and up-regulation of alpha 7 nicotinic receptor protein in transgenic mice co-expressing mutant human presenilin 1 and amyloid precursor proteins. *J Biol Chem*. 2002 Jun. 21; 277(25):22768-80

Mice are cardiac-perfused with phosphate buffered saline (10 mM NaHPO4, 150 mM NaCl, pH 7.2) and fixed with 4% paraformaldehyde. Frozen brain sections are sectioned coronally at a 12-μm thickness using a cryostat, mounted on ProbeOn Plus microscope slides (Fisher Scientific), and air-dried. Immediately before staining, the brain sections are fixed with acetone. Tissue sections are incubated for 30 minutes in 0.3% H2O2 and 0.3% normal goat serum, washed in phosphate-buffered saline, and incubated with 1.5% normal goat serum in phosphate-buffered saline for 30 minutes. Brain sections are then incubated with anti-Aβ antibody 6E10 (1:1000, Senetik) stained with biotinylated anti-mouse IgG (1:200, Vector Laboratories), and immunodetected with Vectastain ABC Reagent (1:100, Vector Laboratories). Sections are counter-stained with hematoxylin.

While a number of embodiments of this invention are described hereinabove, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

We claim:
1. A compound of formula I:

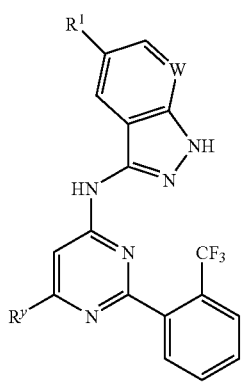

or a pharmaceutically acceptable salt thereof, wherein:
W is CH;
$R^1$ is selected from hydrogen or fluorine; and
$R^y$ is a $C_{1-4}$ aliphatic group, optionally substituted with $N(R^2)_2$ or a 5-6 membered saturated ring having 1-2 heteroatoms independently selected from nitrogen, oxygen, or sulfur, wherein:

each $R^2$ is independently selected from hydrogen or a $C_{1-3}$ aliphatic group optionally substituted with OH, $N(R^3)_2$, or a 5-6 membered saturated ring having 1-2 heteroatoms independently selected from nitrogen, oxygen, or sulfur; and wherein:
each $R^3$ is independently selected from hydrogen or a $C_{1-3}$ aliphatic group;
provided that:
when $R^1$ is hydrogen and W is CH, then $R^y$ is other than methyl.

2. The compound of claim 1, wherein $R^y$ is a $C_{1-4}$ aliphatic group.

3. The compound of claim 2, wherein $R^y$ is selected from methyl, ethyl, cyclopropyl, tert-butyl, or isopropyl.

4. The compound according to claim 3, wherein $R^y$ is selected from methyl, cyclopropyl, or tert-butyl.

5. The compound according to claim 1, wherein $R^1$ is hydrogen.

6. The compound according to claim 1, wherein $R^1$ is fluorine.

7. The compound according to claim 1, wherein $R^y$ is a $C_{1-4}$ aliphatic group substituted with a 6-membered saturated ring having 1-2 heteroatoms independently selected from nitrogen, oxygen, or sulfur.

8. The compound according to claim 7, wherein $R^y$ is a $C_{1-4}$ aliphatic group substituted with a morpholinyl, piperidinyl, or piperazinyl ring.

9. The compound according to claim 1, wherein $R^y$ is a $C_{1-4}$ aliphatic group substituted with $N(R^2)_2$.

10. A compound selected from the group consisting of:

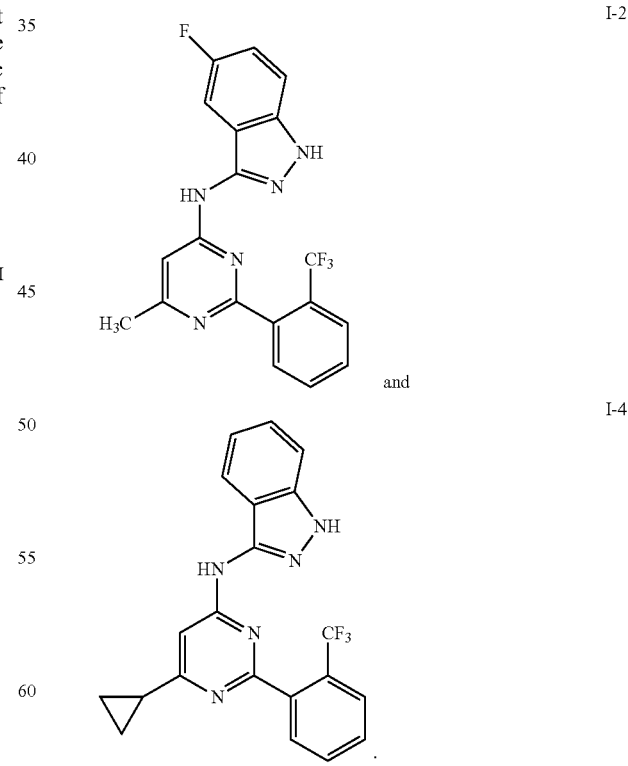

11. A pharmaceutically acceptable composition comprising a compound according to claim 1, and a pharmaceutically acceptable carrier, adjuvent, or vehicle.

12. The composition according to claim 11, additionally comprising an additional therapeutic agent selected from a neurotrophic factor, an agent for treating stroke, an antidepressant, an anti-psychotic agent, or an agent for treating diabetes.

13. A method of treating a disease, disorder, or condition selected from diabetes, schizophrenia, anxiety, bipolar disorder, a spinal cord or peripheral nerve injury, depression, or stroke, in a patient in need thereof, comprising administering to said patient a compound according to claim 1 or a composition according to claim 11.

14. The method according to claim 13, comprising the additional step of administering to said patient an additional therapeutic agent selected from a neurotrophic factor, an agent for treating stroke, an antidepressant, an anti-psychotic agent, or an agent for treating diabetes, wherein:

said additional therapeutic agent is appropriate for the disease being treated; and said additional therapeutic agent is administered together with said composition as a single dosage form or separately from said composition as part of a multiple dosage form.

* * * * *